US008744588B2

(12) United States Patent
Midani et al.

(10) Patent No.: US 8,744,588 B2
(45) Date of Patent: Jun. 3, 2014

(54) METHOD AND SYSTEM FOR CONNECTING AN IMPAIRED NERVOUS SYSTEM TO A MUSCLE OR A GROUP OF MUSCLES BASED ON TEMPLATE MATCHING AND INTELLIGENT END POINTS

(76) Inventors: Hani Midani, West Sand Lake, NY (US); Mowaffak Midani, Naperville, IL (US)

( * ) Notice: Subject to any disclaimer, the term of this patent is extended or adjusted under 35 U.S.C. 154(b) by 1063 days.

(21) Appl. No.: 12/775,072

(22) Filed: May 6, 2010

(65) Prior Publication Data

US 2010/0286748 A1    Nov. 11, 2010

Related U.S. Application Data

(60) Provisional application No. 61/176,171, filed on May 7, 2009.

(51) Int. Cl.
| | |
|---|---|
| *A61N 1/36* | (2006.01) |
| *A61F 2/72* | (2006.01) |
| *B25J 9/00* | (2006.01) |
| *A61B 5/04* | (2006.01) |
| *A61B 5/00* | (2006.01) |
| *A61F 2/70* | (2006.01) |
| *A61B 18/00* | (2006.01) |

(52) U.S. Cl.
CPC ............. *A61N 1/36003* (2013.01); *A61F 2/72* (2013.01); *A61F 2002/704* (2013.01); *A61H 2230/085* (2013.01); *B25J 9/0006* (2013.01); *A61B 5/04001* (2013.01); *A61B 5/7246* (2013.01); *A61B 2018/00839* (2013.01)
USPC .............................................. 607/48; 623/25

(58) Field of Classification Search
CPC .. A61B 5/04888; A61F 2/72; A61F 2002/704
See application file for complete search history.

(56) References Cited

U.S. PATENT DOCUMENTS 7,209,788 B2 *   4/2007   Nicolelis et al. ................. 607/48

FOREIGN PATENT DOCUMENTS

EP   0 421 780 A2 *   4/1991   ................ A61F 2/72

OTHER PUBLICATIONS

Fetz; Volitional control of neural activity: implications for brain-computer interfaces. J. Physiol. 2007; 579; pp. 571-579.
Donoghue et al.; Assistive technology and robotic control using motor cortex ensemble-based neural interface systems in humans with tetraplegia; J. Physiol. 2007; 579; pp. 603-611.
Wolpaw; Brain-computer interfaces as new brain output pathways; J. Physiol. 2007, 579.3; pp. 613-619.

(Continued)

*Primary Examiner* — David H Willse
(74) *Attorney, Agent, or Firm* — Schmeiser, Olsen & Watts, LLP

(57) ABSTRACT

A method and system for connecting an impaired nervous system of a patient to a destination target of a muscle, group of muscles, or robotic device. A command module implanted within the patient's body: (i) samples analog electrical neural signals generated by neurons or nerve fibers of the patient; (ii) processes the neural signals to generate spatial digital data in sample matrices; (iii) processes multiple consecutive sample matrices in real time using sliding window method to generate a time dependent window matrix; (iv) and matches the window matrix to source movement templates to generate high-level movement command(s) which is wirelessly transmitted to driver module(s) within the patient's body and attached to the destination target. The driver module matches the high-level movement commands to destination movement templates to generate a digital stimulus. The digital stimulus is translated into an electrical stimulus which is applied to the destination target.

20 Claims, 10 Drawing Sheets

(56) References Cited

OTHER PUBLICATIONS

Tecchio et al.; Functional source separation and hand cortical representation for a brain-computer interface feature extraction; J. Physiol. 580.3 (2007); pp. 703-721.

Shoham et al.; Statistical Encoding Model for a Primary Motor Cortical Brain-Machine Interface; IEEE Transactions on Biomedical Engineering, vol. 52, No. 7, Jul. 2005; pp. 1312-1322.

Wolpaw and McFarland; Control of a two-dimentional movement signal by a noninvasive brain-computer interface in humans; The National Academy of Sciences of the USA; Dec. 21, 2004, vol. 101, No. 51, pp. 17849-17854. www.pnas.org/cgi/doi/10.1073/pnas.0403504101.

Yoo and Durand; The Recording Properties of a Multi-Contact Nerve Electrode as Predicted by a Finite Model of the Canine Hypoglossal Nerve; Proceedings of the 26th Annual International Conference of the IEEE EMBS San Francisco, CA, USA, Sep. 1-5, 2004; pp. 4310-4313.

BrainGate—"About" and "Technology" Tabs (from website). [online]. 2 pages. [retrieved on May 6, 2010]. Retrieved from the Internet:< URL: www.cyberkineticsinc.com>.

\* cited by examiner

METHOD AND SYSTEM FOR CONNECTING AN IMPAIRED NERVOUS SYSTEM TO A MUSCLE OR A GROUP OF MUSCLES BASED ON TEMPLATE MATCHING AND INTELLIGENT END POINTS

RELATED APPLICATION

This application claims priority to U.S. Provisional Application No. 61/176,171, filed May 7, 2009, which is incorporated by reference herein in its entirety.

FIELD OF THE INVENTION

The present invention provides a method and system for connecting an impaired nervous system to a muscle or a group of muscles based on the concepts of template matching and intelligent end-points.

BACKGROUND OF THE INVENTION

Injuries may occur at any level of the nervous system in the brain, the spinal cord, the peripheral nerves or the muscles. Even a focal lesion in the nervous system may interrupt neural connections and lead to loss of function such as paralysis, despite the fact that the remaining neural connections are still functional Research in the area of neuroscience, Brain-computer Interface (BCI), and Brain-Machine Interface (BMI) is directed to the use of electrical signals detected at the nervous system to produce movements or other actions at a limb bypassing areas of nervous system damage. See E. Fetz, Volitional control of neural activity: implications for brain-computer interfaces, J. Physiol. 2007, 579; 571-579. See, also, J. Donoghue, A. Nurmikko, et al., Assistive technology and robotic control using motor cortex ensemble-based neural interface systems in humans with tetraplegia, J. Physiol. 2007, 579; 601-611. See, also, J. Wolpaw, Brain-computer interfaces as new brain output pathways, J. Physiol. 2007, 579; 613-619.

Simple movement and direct control of prosthetic arm and paralyzed muscle by cortical neurons was done in monkeys. See M. Velliste et al., Cortical control of a prosthetic arm for self-feeding, Nature 2008, 453; 1098-1101. See, also, C. Moritz, S Perlmutter and E Fetz, Direct control of paralyzed muscles by cortical neurons, Nature 2008, 456; 639-642.

Neural control of prosthetic device was also done in humans with neurological motor disability. See L Hochberg et al., Neural ensemble control of prosthetic devices by a human with tetraplegia, Nature 2006, 422; 164-171.

Unfortunately, current systems for restoring neural connections lack efficient mobility, portability, and adaptability needed for use by humans.

SUMMARY OF THE INVENTION

The present invention provides a method for connecting an impaired nervous system of a patient to a destination target, said method comprising:

a command module sampling analog electrical neural signals over time at a sampling period, said neural signals having been generated by neurons or nerve fibers of the patient and having been sampled at each spatial location of a plurality of spatial locations within the patient's body, said command module being a first device implanted within the patient's body;

said command module processing the sampled analog electrical neural signals to generate digital data specific to the spatial locations;

said command module using a sliding window process to generate a sliding window which advances in time in step with the sampling period, said sliding window having a sliding window time duration that exceeds the sampling period, said sliding window encompassing the digital data over the sliding window time duration;

said command module processing the digital data in the sliding window to generate a window matrix, each element of the window matrix comprising parameters relating to electrical spiking/discharge activity at the spatial locations over the sliding window time duration;

said command module matching the parameters in the window matrix to stored information in source movement templates to generate at least one high-level movement command relating to electrically activating the destination target, said destination target being a muscle of the patient, a group of muscles of the patient, or a robotic device;

wirelessly transmitting the at least one high-level movement command to at least one driver module at a command transmission interval of time that exceeds the sampling period and is less than the sliding window time duration, said at least one driver module being at least one second device implanted within the patient's body and attached to the destination target;

said at least one driver module matching the at least one high-level movement command to destination movement templates to generate at least one digital stimulus;

said at least one driver module translating the at least one digital stimulus into at least one electrical stimulus;

said at least one driver module applying the at least one electrical stimulus to the destination target, which activates the destination target.

The present invention provides a neuro-bridge system comprising a command module and at least one driver module, said system configured to implement a method for connecting an impaired nervous system to a destination target, said method comprising:

said command module sampling analog electrical neural signals over time at a sampling period, said neural signals having been generated by neurons or nerve fibers of the patient and having been sampled at each spatial location of a plurality of spatial locations within the patient's body, said command module being a first device implanted within the patient's body;

said command module processing the sampled analog electrical neural signals to generate digital data specific to the spatial locations;

said command module using a sliding window process to generate a sliding window which advances in time in step with the sampling period, said sliding window having a sliding window time duration that exceeds the sampling period, said sliding window encompassing the digital data over the sliding window time duration;

said command module processing the digital data in the sliding window to generate a window matrix, each element of the window matrix comprising parameters relating to electrical spiking/discharge activity at the spatial locations over the sliding window time duration;

said command module matching the parameters in the window matrix to stored information in source movement templates to generate at least one high-level movement command relating to electrically activating the destination target, said destination target being a muscle of the patient, a group of muscles of the patient, or a robotic device;

wirelessly transmitting the at least one high-level movement command to said at least one driver module at a command transmission interval of time that exceeds the sampling period and is less than the sliding window time duration, said at least one driver module being at least one second device implanted within the patient's body and attached to the destination target;

said at least one driver module matching the at least one high-level movement command to destination movement templates to generate at least one digital stimulus;

said at least one driver module translating the at least one digital stimulus into at least one electrical stimulus;

said at least one driver module applying the at least one electrical stimulus to the destination target, which activates the destination target.

The present invention advantageously provides an efficient mobile, portable, and adaptable method and system for connecting an impaired nervous system to a muscle or a group of muscles.

DETAILED DESCRIPTION OF THE INVENTION

Figure 1:
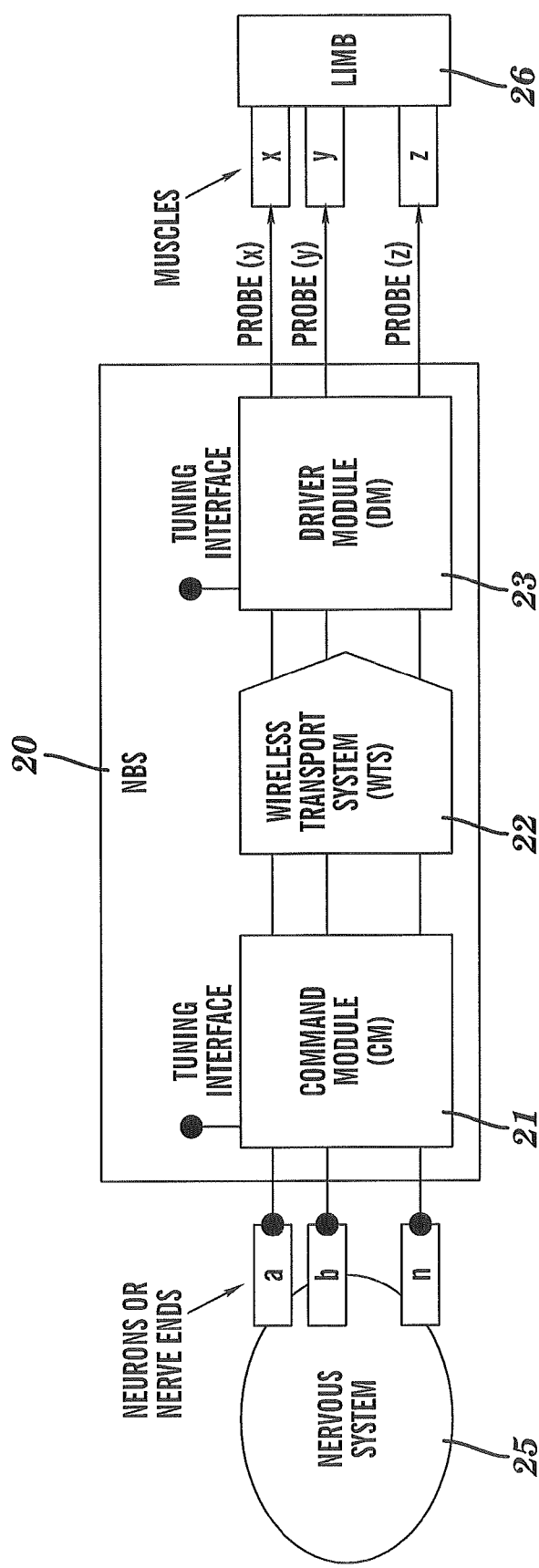
FIG. 1 depicts basic components of the Neuro-Bridge System (NBS), in accordance with embodiments of the present invention.

The present invention provides a method and associated Neuro-Bridge System (NBS) for connecting impaired nervous system to organs (i.e. muscles) or instruments (i.e. robotic device/electronic device) over a command-based digital wireless transport apparatus. NBS includes a miniature neuro-electrical apparatus that can be implanted in the human body. NBS allows a patient who sustained injury to his/her nervous system to regain some level of control over a target organ such as limb muscles or a robotic instrument or an electronic instrument. NBS interfaces with the nervous system to receive stimulus and generate high-level movement commands for transport over a wireless link to interface with the target organs or instruments. NBS is based on the principles of intelligent end-points, source movement templates, destination movement templates, a sliding window method for analyzing sampled analog electrical neural signals over time and template matching.

The detailed description of the present invention is organized into the following sections:
1. Measurement of Neural Activity
2. Introduction to Neuro-Bridge System (NBS)
3. High-level System Decomposition
4. Logical Flows at the Source and Destination
5. Data Sampling and Collection Method
6. Data Representation in NBS
7. Movement Analysis
8. Templates and Relation to Movement Commands
9. Creation and Use of Templates
10. High Level Movement Commands (HLMC)
11. Data Representation and the High Level of Abstraction
12. Aspects of the Neuro-Bridge System
13. Features of the Present Invention
14. Method For Connecting an Impaired Nervous System To Muscle(s)

1. Measurement of Neural Activity

The present invention provides a method and system for connecting an impaired nervous system to a muscle or a group of muscles and/or to an organ of a patient or an instrument.

Motor commands originate at the cerebral motor cortex. In the motor cortex there are nerve cells called the Upper Motor Neurons (UMN). The UMNs are the main source of cortical motor command output to other motor centers in the central nervous system. The UMNs connect directly to other nerve cells in the spinal cord called the Lower Motor Neurons (LMN). A complex process of feedback and modulation of neural signals takes place between the UMNs and the LMNs. Peripheral motor Nerve Fibers (NF) originate from the LMNs and connect directly with their target organ, the muscle fibers. The cell membrane of a NF is an extension of the cell membrane of the neuron of origin. The entire nervous system is somatotopically organized. That means that the body or target organ is precisely spatially represented in the nervous system at all levels from the cortex to the peripheral nerves. Therefore, it is possible to identify and match groups of motor neurons and motor nerve fibers with their target muscle fibers When the nerve cell is excited, an electrical discharge develops called action potential. This action potential can be recorded in the form of a "spike" inside of the brain using recording electrodes inserted in the cortex. With recording on the surface of the cortex known as electrocorticography (ECoG) event related potentials (ERP) are recorded which reflect the sum of multiple spikes in the area of recording.

Neuronal discharge patterns in the motor cortex and its connections correlate with specific motor plans and intentions, which provides a rich source of movement information. See W. T. Thach, Correlation of neuronal discharge with pattern and force of muscular activity, joint position, and direction of intended next movement in motor cortex and cerebellum, Journal of Neurophysiology 1978, 41; 654-676.

Another form of electrical potentials is the Local Field Potential (LFP). This represents the summation of electrical activity of a cortical area excluding spike activity. The spike activity is filtered with a low-pass filter. LFP may provide additional useful information. Neuronal action potentials from the brain can be measured.

By using different band-pass filtering, such measurements can record multiple forms of electrical potentials including single- or multi-neuron spiking as well as lower frequency ERP and LFPs.

Information related to spiking appears mainly to be carried in the spike rate typically measured as the number of spikes within a defined interval (e.g. count in a 50 ms bin). Although some other aspects of spiking such as relative timing (synchronization or coherence between multiple UMNs) may also carry significant information. Spiking frequency and pattern modulate various parameters of movement such as speed, direction, and force of movement. Thus each of these parameters represents useful control signals. ERP and LFP are measured in frequency domains. Several frequency domains are used for classification. The bands of most interest are Alpha and Mu (8-12 Hz), Beta (13-25 Hz) and Gamma (50-300 Hz).

As to amplitude input, the amplitude of neuronal spike has a fixed value under stable recording conditions. Amplitude measurement using multiple trigger thresholds will allow the identification and correlation of spike activity with specific neuronal population.

As to frequency input, neuronal firing frequency varies and correlates with the cortical events. High frequency discharges (Gamma band) is of special interest for ECoG recording.

As to configuration input, a spike or ERP that is close to a recording electrode has higher amplitude, steeper rise slope and short duration. A more distant spike or ERP has lower amplitude, less steep rising slope and longer duration. A potential recorded from multiple UMNs firing synchronously and equidistant from the recording electrode will summate into a higher amplitude. If the UMNs are not synchronous, or are not equidistant from the recording electrode, the potential will have lower amplitude and longer duration. A neuronal ensemble will generate stable potential configuration under stable activation and recording conditions.

As to pattern input, neuronal firing pattern is predictable and reproducible. The same neuronal ensemble will fire in a predictable pattern when performing the same simple movement. For more complex and dynamic movements, many neuronal ensembles will be recruited according to a certain order specific to the motor task. This larger scale pattern is reproducible and predictable for the specific motor task.

As to temporal and spatial relationships input, for a simple low force movement, certain population of UMN will fire at low frequency. With increased force demand, firing frequency will increase; hence, temporal recruitment. Once the firing UMN reach a critical firing frequency, other UMN are recruited; hence, spatial recruitment. This is a neuronal ensemble that works together to command a simple movement. More complex movements require the function of multiple neuronal ensembles according to an order specific to the intended movement. Consequently, the measured data is multi-dimensional and complex.

2. Introduction to Neuro-Bridge System

The Neuro-Bridge System (NBS) uses a novel approach to transmit neural information between two points in the nervous system bridging an area of damage. NBS approach is based on the principles of two intelligent end points, source movement templates, destination movement templates, and Neuro-Bridge sliding window method.

NBS's high level of data abstraction represents the brain/nervous system activities numerically via the sample matrix and the window matrix. NBS uses Neuro-Bridge movement templates for determining typical movement commands. These templates are tuned and customized by the physician at the time of implantation (or afterward) for better results.

The Neuro-Bridge sliding window method collects, extracts, and analyzes neural information in spatial and temporal dimensions and then generates high-level commands based on real-time matching of neural measurements with customized movement templates. The commands are transported over a secure and encrypted wireless link between the intelligent end points (source and destination).

This system allows for the bypassing of the damaged area in the nervous system to drive the target organ with much higher efficiency, mobility, and adaptability than current systems.

3. High-Level System Decomposition

FIG. 1 depicts basic components of the Neuro-Bridge System (NBS) 20, in accordance with embodiments of the present invention. The basic components of NBS 20 comprise or consist of the Command Module (CM) 21, the Wireless Transport System (WTS) 22, and the Driver Module (DM) 23.

The Command Module (CM) 21 attaches to the nervous system 25 and collects patterns of neural signals in the form of electrical potentials generated by neurons or nerve fibers. The Command Module 21 then converts the action potentials to coded digital signals, creates spatial and temporal representation of the neural patterns, performs pattern recognition based on a newly proposed sliding window method and movement templates that are uniquely adapted to the needs of the patient, and generates corresponding high-level movement commands.

The Wireless Transport System (WTS) 22 transmits high-level movement commands from the command module 21 to the destination driver module 23 over a wireless medium.

The Driver Module (DM) 23 attaches to the muscles of the limb 26 or the robotic/electronic device. The Driver Module 23 receives high-level movement commands and converts the high-level movement commands to an electrical stimulus based on patient-tuned and adapted destination movement templates, and then delivers the electrical stimulus to the target muscles or robotic/electronic device.

In one embodiment, there are multiple NBSs implanted in the human body operating independently and simultaneously over a wireless transport network. Proper communication and message addressing is incorporated in the system design to allow the movement commands to be sorted out at the destination.

In one embodiment, for a single NBS implanted in the human body, there are multiple Driver Modules controlled by a single Command Module to operate/stimulate multiple muscles. Proper communication and message addressing is incorporated in the system design to allow the movement commands from a single source to reach the proper destination.

In one embodiment, NBS provides tuning interfaces to optimize the system, where a tuning interface is provided for each command module and a tuning interface is provided for each driver module. This system feature allows the physician to tune the system parameters to better fit the patient's needs and to optimize system's performance. Initial tuning will take place at the time of implantation, followed by an ongoing training to achieve more complex movements.

The Command Module 21, the Wireless Transport System 22, and the Driver Module 23 are described next in greater detail.

3.1 Command Module (CM)

Figure 2:
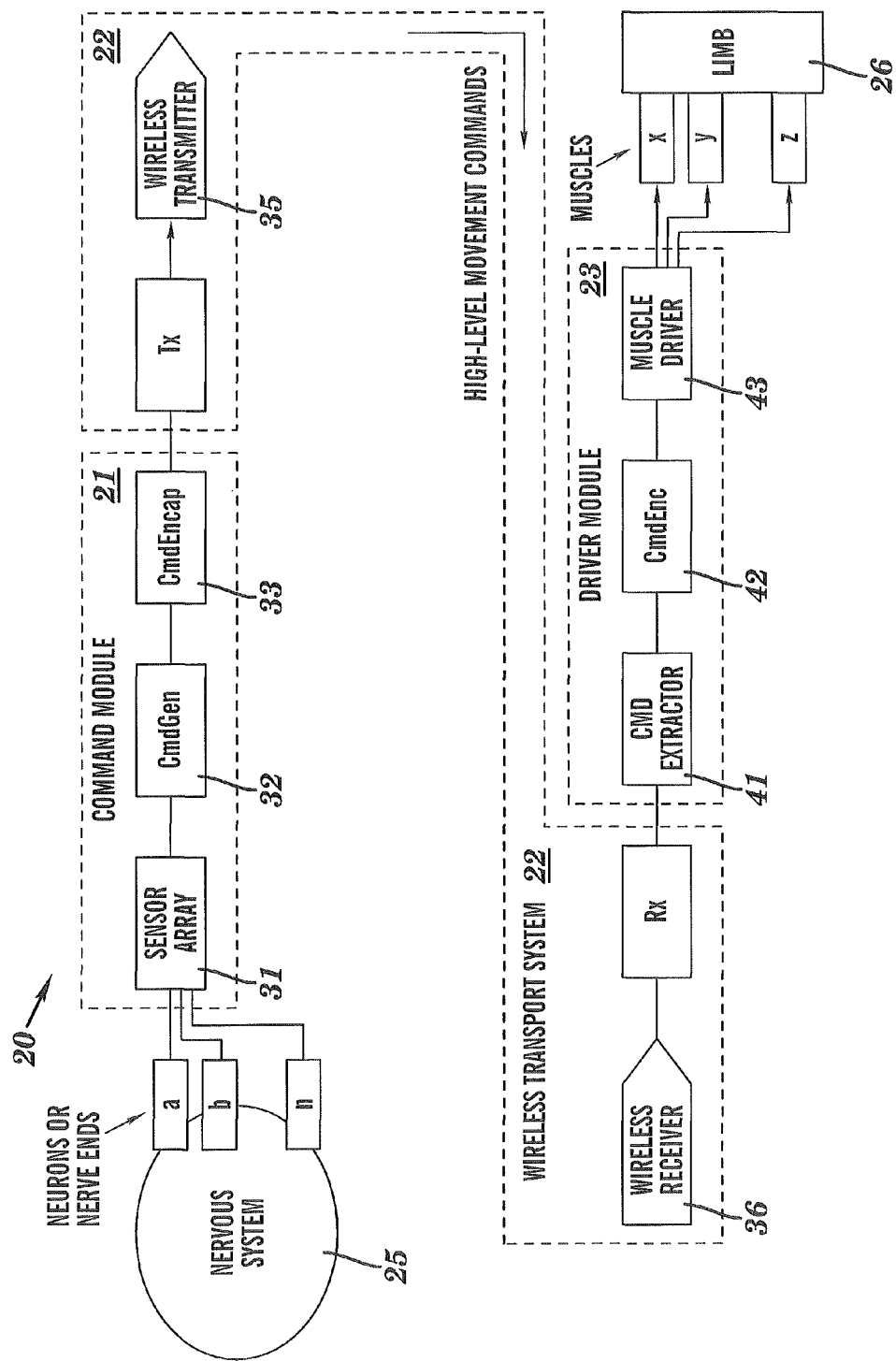
FIG. 2 depicts a detailed decomposition of the NBS with its main modules and components, in accordance with embodiments of the present invention.

FIG. 2 depicts a detailed decomposition of the NBS 20 with its main modules and components, in accordance with embodiments of the present invention.

The Command Module (CM) 21 comprises or consists of a Sensor Array 31, a Command Generator 32, and a Command Encapsulator 33.

The Sensor Array (SA) 31 is implanted in the nervous system and captures analog electrical neural signals generated by the neurons or nerve fibers. There may be multiple physical sensor arrays implanted in the human body as part of a command module to cover a wider area of the nervous system.

The Command Generator (CmdGen) 32 generates high-level movement commands.

The measured electrical neural signals from a single sensor array or multiple sensor arrays are digitized, processed, and stored in two matrices, namely the Sample Matrix and the Window Matrix which enables NBS 20 to capture information about neural firing activities in both the spatial and temporal domains that are then compared with already stored and tuned source movement templates (SMT). Once the comparison is completed High-Level Movement Commands (HLMCs) are generated.

Movement commands are generated and sent at regular time intervals, each time interval being called a Command Transmission Interval (CTI). A particular movement command has an impact for duration of CTI (e.g., in msec) reflecting a specific piece-wise micro-movement event. Continuity is kept by making sure that commands are sent every CTI, if a movement action is determined.

In one embodiment, a system-wide CTI may be chosen for NBS with a recommended sampling time (i.e., sampling period) of 1 msec and a CTI value of 10 msec, which allows the system to consider 10 samples before making a definite decision about a particular micro-movement and then sending the next HLMC over the wireless link.

The Command Encapsulator (CmdEncap) 33 generates unique source and destination addresses and encapsulates movement commands in transmission packets.

In one embodiment, the Command Module (CM) 21 uses multiple physical sensor arrays to capture neural activities over a wider cortical area. The Command Module (CM) 21 will take into account the entirety of the collected data to produce the corresponding movement commands.

3.2 Wireless Transport System

The Wireless Transport System 22 comprises a Packet Transmitter 35 and a Packet Receiver 36. The Packet Transmitter 35 that transmits packets over a secure short-range wireless transmission system. All packets are transmitted over a specified frequency band over the shared physical wireless medium. The Packet Receiver 36 receives packets over a secure short-range wireless transmission system over the specified frequency.

3.3 Driver Module

The Driver Module 23 comprises or consists of Command Extractor 41, Command Encoder 42, and Muscle Driver 43.

Command Extractor (CmdExtractor) 41 intercepts/captures only the packets with the correct destination address and security keys.

Command Encoder (CmdEnc) 42 translates high-level movement commands (HLMCs) based on stored destination movement templates, and locally generates corresponding digital destination patterns.

Muscle Driver 43 (or robotic/electronic device) generates, based on the generated digital destination patterns, analog electrical stimulus via electric probes to stimulate the target muscles or robotic/electronic devices.

HLMCs are generated by the command module and sent to the driver module every CTI to induce a movement action. In turn, the driver module applies the corresponding electrical stimulus via its probes for the duration of the CTI, according to the electrical specifications described in the destination movement template and the movement intensity factor in the HLMC.

In one embodiment, multiple driver modules are part of a single NBS. Each NBS with its muscle driver stimulates a muscle or group of muscles of which all are controlled by a single command module. In this case, corresponding movement commands are sent from the command module to each of the driver modules.

4. Logical Flows at the Source and Destination

Figure 3:
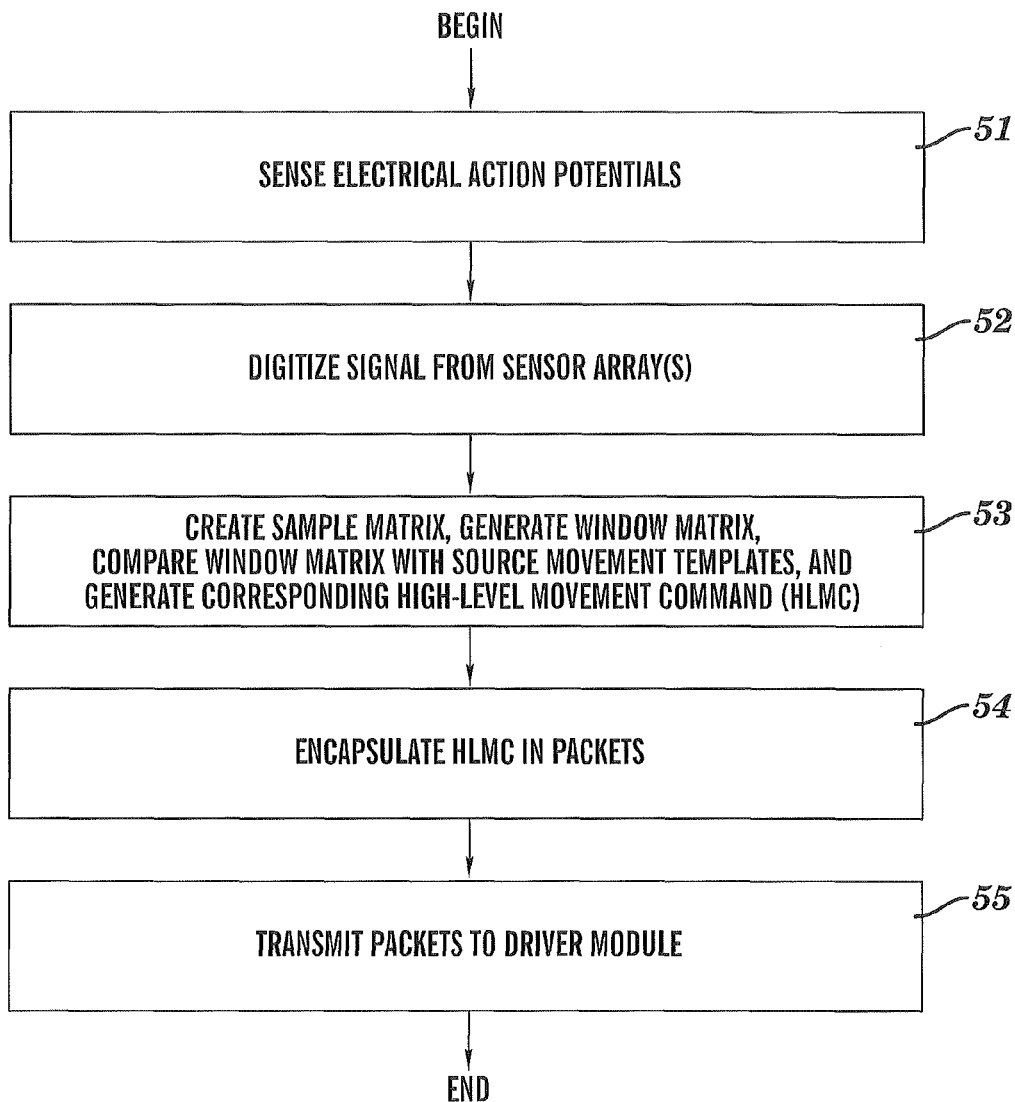
FIG. 3 is a flow chart depicting logical flow executed by NBS at the Command Module, in accordance with embodiments of the present invention.
Figure 4:
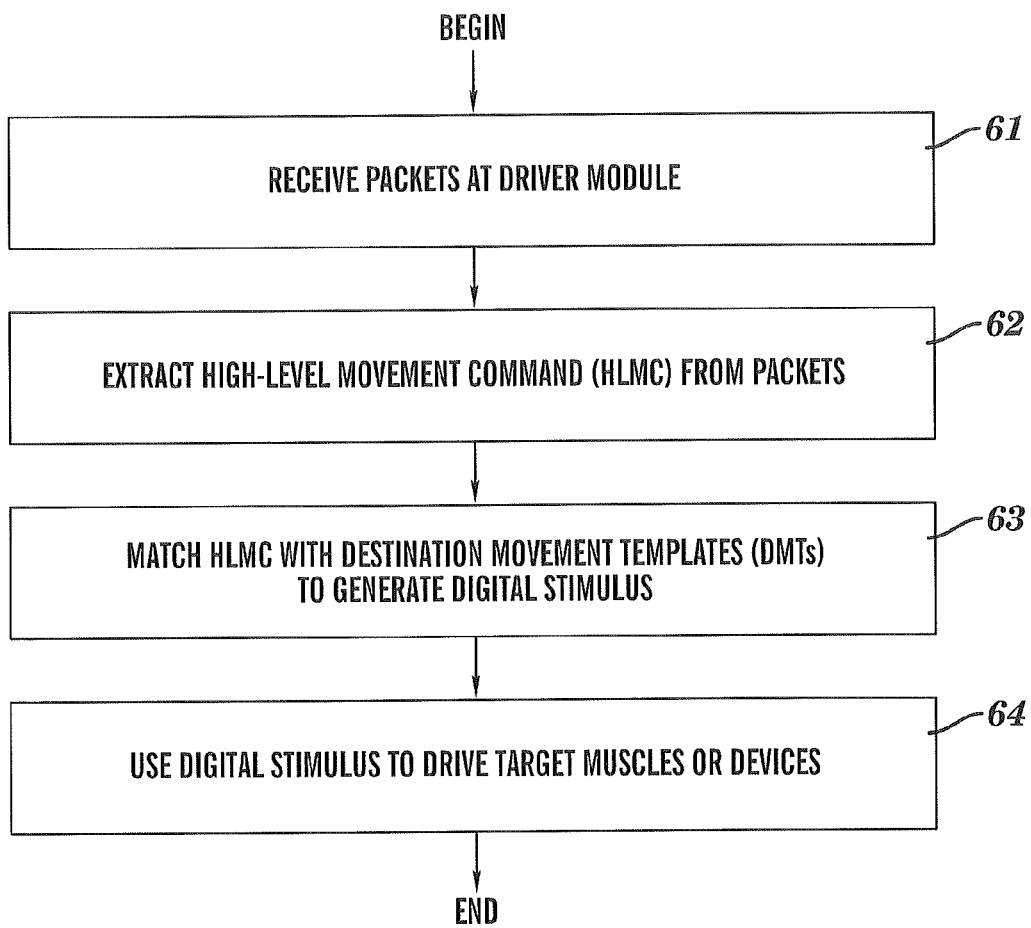
FIG. 4 is a flow chart depicting logical flow executed by NBS at the Driver Module, in accordance with embodiments of the present invention.

NBS 20 executes logical flow at the Command Module 21 (FIG. 3) and at the Driver Module 23 (FIG. 4).

FIG. 3 is a flow chart depicting logical flow executed by NBS 20 at the Command Module 21, in accordance with embodiments of the present invention. The logical flow in FIG. 3 comprises steps 51-55.

In step 51, Command Module (CM) 21 senses electrical action potentials from multiple neurons or nerve fibers using sensor arrays 31.

In step 52, Command Module 21 digitizes the signal from the sensor array(s) 31, taking into account the spatial relationship between the sensors and the neurons or nerve fiber.

In step 53, Command Module 21 generates the sample matrix every sample time, analyzes the measured data and creates the window matrix, compares the window matrix with previously stored and tuned source movement templates (SMTs) using best-match algorithm in one embodiment, and generates the corresponding high-level movement command (HLMC). The source movement templates (SMTs) are tuned during a training phase.

In step 54, Command Module 21 encapsulates the HLMC in packet(s), with proper addressing information and security measures.

In step 55, Command Module 21 sends packets over short range wireless transport system.

FIG. 4 is a flow chart depicting logical flow executed by NBS 20 at the Driver Module 23, in accordance with embodiments of the present invention. The logical flow in FIG. 4 comprises steps 61-64.

In step 61, Driver Module (DM) 23 receives the packet(s) sent in step 55 of FIG. 4 over short range wireless transport system 22.

In step 62, Driver Module 23 captures the packets, based on packet addressing information, and extracts the high-level movement command (HLMC).

In step 63, Driver Module 23 matches the received HLMC with its corresponding destination movement template(s) (DMTs), and generates the digital stimulus. The destination movement templates (SMTs) are tuned during a training phase.

In step 64, Driver Module 23 translates the digital stimulus into electrical action potentials that are applied via electric probes to drive the target muscles or device(s).

5. Data Sampling and Collection Method

In one embodiment, neural data is collected from one or more sensor arrays 31 (see FIG. 2). After reading and incorporating the measurements from the recording electrodes of the sensor arrays 31, the data may be cleaned up and pruned via a variety of available filtering techniques.

In one embodiment, collected data is processed based on a sliding window method that allows for the extraction of temporal and spatial information from the measured electrical data.

In one embodiment, the sampling period is defined as the time between two consecutive samplings of neural activity at the source. For the sake of simplicity and without any loss of generality, this assumes that the system will take a snapshot measurement every 1 millisecond (in one embodiment) to generate a snapshot worth of information that will be numerically represented in a matrix termed the Sample Matrix $A_S$, described below. The sliding window is defined as the view of a specific time duration "n", of data collected and processed from a specific number of previously collected consecutive samples. Without any loss of generality, if the sliding window duration is 50 msec, and if the sampling period is 1 msec, then every 1 msec NBS analyzes and processes the latest measured data sample and the previous 49 samples for each recording electrode, as represented by the Sample Matrix $A_S$ for each sample, to generate the corresponding neural window information. The duration of the sliding window may be adjustable and determined based on best system performance and movement templates.

Neural temporal and spatial information in a sliding window is organized in a matrix termed the Window Matrix $W_S$, as described infra.

6. Data Representation in NBS 6.1 Sample Matrix $A_S$

The collection of real-time spatial data from all the recording electrodes on each sampling time is organized in the Sample Matrix $A_S$, which is a set of action potential values $$A_s = \begin{pmatrix} a_{11} = (v_{11} \cdot c_{11}) & a_{12} = (v_{12} \cdot c_{12}) & a_{13} = (v_{13} \cdot c_{13}) & a_{14} = (v_{14} \cdot c_{14}) \\ a_{21} = (v_{21} \cdot c_{21}) & a_{22} = (v_{22} \cdot c_{22}) & a_{23} = (v_{23} \cdot c_{23}) & a_{24} = (v_{24} \cdot c_{24}) \\ a_{31} = (v_{31} \cdot c_{31}) & a_{32} = (v_{32} \cdot c_{32}) & a_{33} = (v_{33} \cdot c_{33}) & a_{34} = (v_{34} \cdot c_{34}) \\ a_{41} = (v_{41} \cdot c_{41}) & a_{42} = (v_{42} \cdot c_{42}) & a_{43} = (v_{43} \cdot c_{43}) & a_{44} = (v_{44} \cdot c_{44}) \end{pmatrix}$$

measured on each recording electrode, and the associated weight of each measured value. For example, a 4×4 matrix $A_S$ is represented as follows:

For a single sensor array system, each recording electrode in the array is associated with one element in the matrix shown above. A recording electrode in row i=2 and column j=3 is associated with element $a_{23}$. Each element $a_{ij}$ is the product of two entities: $v_{ij}$ and $c_{ij}$ (i.e., $a_{ij}=v_{ij}*c_{ij}$). The entity $v_{ij}$ is the actual measured potential value at that recording electrode, at that sample (e.g., in units of mV). The entity $c_{ij}$ is the associated coefficient (multiplier/attenuator) for that recording electrode, based on the coefficient matrix $C_S$.

6.2 Coefficient Matrix $C_S$

All the $c_{ij}$ values for a sensor array are stored on the command module in the Sample Coefficient Matrix $C_S$. The default (initial) value for all the $c_{ij}$ elements is 1, which means no change is applied to the measured value.

However, to take into account variability from one person to another, the positioning of the sensor array in the body, and the possibility of noise and interference between recording electrodes, these coefficients $c_{ij}$ can be adjusted or tuned after the sensor array is implanted in the human body. Tuning is performed by the physician during the system tuning stage. The $c_{ij}$ value allows the system to amplify, suppress, or discard the measured reading on a particular recording electrode to account for any noise or other variations.

For example, setting a $c_{ij}$ value to zero means that this recording electrode is being ignored and its data will not be considered in any further analysis, while setting the $c_{ij}$ value to one or more means that the measured value on that recording electrode is to be fully considered.

In another example, if a recording electrode is inserted between a number of nerve ends, then it is possible that this recording electrode might measure an excessive level of noise generated from different sources. If the noise level is high enough to reach, or get close to, the spike/potential threshold, then some suppression can be applied to that recording electrode to make the random noise level safely below the spike/potential threshold. Thus only when a real neuro activity occurs, the potential value on that recording electrode actually crosses the spike/potential threshold.

In another example, the physician may determine that the potential measured on a particular recording electrode is essential or particularly significant, but due to its distance of the recording electrode from the neural source, the signal is too weak. In this case, the corresponding $c_{ij}$ value could be increased to 1.5 or 2.0 in order to increase the relative weight of the potential measured on the particular recording electrode.

For example, for a 4×4 sensor array for which the physician determines that: (i) recording electrodes (1,1), (1,2), (2,1), and (2,2) are to be amplified (i.e., $c_{ij}>1$), (ii) recording electrodes on the fourth column are all to be ignored (i.e., $c_{ij}=0$), and (iii) all other recording electrodes are to be considered with their exact measured value with no attenuation or amplification (i.e., $c_{ij}=1$), then the corresponding illustrative $C_S$ matrix for such a system is as follows:

$$C_s = \begin{pmatrix} 1.5 & 2.0 & 1.0 & 0 \\ 1.1 & 1.3 & 1.0 & 0 \\ 1.0 & 1.0 & 1.0 & 0 \\ 1.0 & 1.0 & 1.0 & 0 \end{pmatrix}$$

There is not one formula for all the recording electrodes and for all patients. The determination of the optimum $c_{ij}$ values and thus the content of the entire sample coefficient matrix $C_S$ will be set on a case by case basis for each implanted sensor array. In one embodiment, the default setting of 1 for each $c_{ij}$ value may be used to initialize the Sample Coefficient Matrix $C_S$.

6.3 Sensor Map Matrix S

For a multi-sensor array system, a virtual sensor array that is made of selected recording electrodes from the multiple sensor arrays is created by the physician/technician. This is accomplished by creating the Sensor Map Matrix S. Each entry (i.e., each sub-matrix) in the S matrix refers to (or maps to) a specific physical sensor array and the recording electrodes respectively associated with the elements of the specific physical sensor array.

Figure 5:
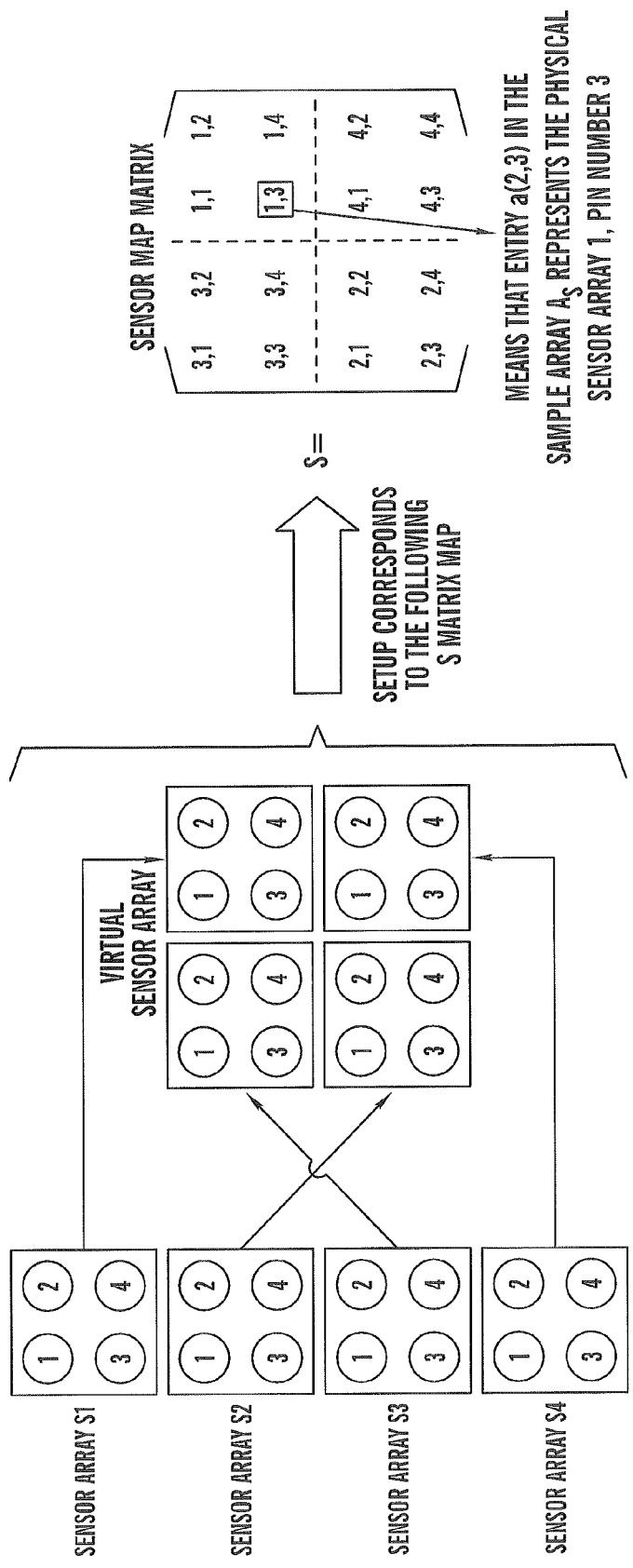
FIG. 5 is an illustrative example of a sensor mapping for a multiple sensor array, in accordance with embodiments of the present invention.

FIG. 5 is an illustrative example of a sensor mapping for a multiple sensor array, in accordance with embodiments of the present invention. In FIG. 5, four sensor arrays S1, S2, S3, and S4 are implanted each with size 2×2, and if the desired sample array size is 4×4, then the sensor mapping matrix S is constructed as depicted in FIG. 5. As shown in FIG. 5, the virtual sensor array is mapped to a 4×4 sensor mapping matrix S consisting of four 2×2 sub-matrices, wherein the four sensor arrays (S1, S2, S3, S4) are loaded into associated 2×2 sub-matrices of the sensor mapping matrix S.

The size of the mapping matrix S must be of the same size of the Sample Matrix $A_S$, and the previous description regarding the definition and handling of the coefficients $C_{ij}$ still applies to the $A_S$ matrix, which is now the representation of the virtual sensor array (rather than the physical sensor array).

6.4 Window Matrix $W_S$

A result of performing spike/potential recognition on a sequence of consecutive Sample Matrices $A_S$ for a sliding window duration "n" will allow for the representation of the temporal neural information such as spike/potential, spike/potential frequency, and spiking/discharge duration.

For Local Field Potential (LFP) and event related potentials (ERP), since no spiking will be observed, the temporal data on the recording electrode will be measured and extracted in terms of maximum, average, and minimum potentials among other attributes within a particular window. Without any loss of generality, these parameters can be added to the $W_S$ Matrix in a future system enhancement and adaptation.

Taking into account the values and weights (coefficients) in consecutive Sample Matrices $A_S$ over a sliding window duration "n" (e.g., n=50 msec), the method of the present invention will run the correlation and feature extraction algorithms in real time to produce the Window Matrix $W_S$ defined as follows:

$$W_s = \begin{pmatrix} w_{11} & w_{12} & w_{13} & w_{14} \\ w_{21} & w_{22} & w_{23} & w_{24} \\ w_{31} & w_{32} & w_{33} & w_{34} \\ w_{41} & w_{42} & w_{43} & w_{44} \end{pmatrix}$$

Each element $w_{ij}$ in the $W_S$ matrix is a multi-dimensional entity $w_{ij}$ defined via $w_{ij}=(a, b, c, d, e, f)$, which is a vector comprising components a, b, c, d, e, and f.

Component "a" is the weight of this element in the matching process, which is equal to the corresponding $c_{ij}$ value in the sample matrix $A_S$, and is based on the corresponding element in the C matrix. If this $c_{ij}$ value is zero, then the measurement obtained from the corresponding recording electrode is ignored in any further processing.

Component "b" is the spike/potential presence indicator on that recording electrode. This is a binary value of "one" or "zero". The value of "one" means that a spike/potential has been detected on this recording electrode within the sliding window. The spike/potential presence indicator component is determined based on the result of running a spike/potential detection algorithm. In its simplest form, such an algorithm tracks the measured values on a particular recording electrode, taking into account the corresponding weight coefficient, over a number of consecutive $A_S$ samples. If the weighted measured values cross (i.e., exceed) the spike/potential threshold repeatedly, up and down, then a spike/potential is declared on that recording electrode within this window. The spike/potential threshold is a system programmable value that depends on the sensor array technology.

Component "c" is the spike/potential frequency in Hz, if spiking/discharge activity is detected/recognized in this sliding window on that recording electrode. In general, this represents the dominant recognized frequency band (in Hz), such as the gamma band signal, or specific dominant frequencies of a compound multi-frequency signal within a frequency band.

Component "d" is the spiking/discharge duration in msec, if spiking/discharge activity is detected/recognized in this sliding window duration on that recording electrode. Spiking/discharge activity duration may be smaller or equal to the sliding window duration. In other words, maximum spiking/discharge duration, per window, cannot exceed the sliding window duration (e.g., 50 msec). The next $W_S$ matrix will pick up from where the previous $W_S$ matrix left off, in time. Since a new movement command is sent every CTI, where CTI is less than the Window duration, time continuity is preserved by NBS system.

Component "e" is the sub-threshold potential value representing the summation of LFPs in mV on that recording electrode.

Component "f" is the sub-threshold potential duration, if recognized by the extraction algorithm on that recording electrode.

The first four components of: a (weight), b (spike/potential presence), c (spike/potential frequency), and d (spiking/discharge duration), form the basic set of data for the next step in determining the desired movement command. The last two components, e (sub-threshold potential value) and f (sub-threshold potential duration), are secondary factors and are for further study.

The following illustrative Window Matrix $W_S$ is of size 4×4 at a particular sampling time.

$$W_s = \begin{bmatrix} w_{11}=(1,0,0,0,0,0) & w_{12}=(1,1,30,10,0,0) & w_{13}=(1,0,0,0,0,0) & w_{14}=(1,0,0,0,0,0) \\ w_{21}=(1,0,0,0,0,0) & w_{22}=(1,1,40,10,0,0) & w_{23}=(1,1,20,20,0,0) & w_{24}=(1,0,0,0,0,0) \\ w_{31}=(1,0,0,0,0,0) & w_{32}=(1,1,100,50,0,0) & w_{33}=(1,1,30,50,0,0) & w_{34}=(1,0,0,0,0,0) \\ w_{41}=(1,0,0,0,0,0) & w_{42}=(1,0,0,0,0,0) & w_{43}=(1,1,30,50,0,0) & w_{44}=(1,0,0,0,0,0) \end{bmatrix}$$

Pattern of interest

In the preceding illustrative Window Matrix $W_S$, the first, second, third, and fourth digits of each element $w_{ij}$ represent the weight, spike/potential presence, spike/potential frequency, and spiking/discharge duration within that window respectively. The fifth and sixth digits represent the sub-threshold potential and sub-threshold potential duration, respectively, with zero values for this example. Thus, the recording electrodes corresponding to the elements in the fourth column ($w_{14}, w_{24}, w_{34}, w_{44}$) are all to be ignored, since their coefficient values $c_{ij}$ were all set to zero in the illustrative $C_S$ matrix presented supra. Only 6 of the other 12 recording electrodes detected spiking/discharge activities during window with the following extracted information.

Recording electrode (1,2) is detecting spiking/discharge activity at 30 Hz which has been going on for a duration of 10 msec.

Recording electrode (2,2) is detecting spiking/discharge activity at 40 Hz which has been going on for a duration of 10 msec.

Recording electrode (2,3) is detecting spiking/discharge activity at 20 Hz which has been going on for a duration of 20 msec.

Recording electrode (3,2) is detecting spiking/discharge activity at 100 Hz which has been going on for a duration of 50 msec (sliding window duration).

Recording electrode (3,3) is detecting spiking/discharge activity at 30 Hz which has been going on for a duration of 50 msec (sliding window duration).

Recording electrode (4.3) is detecting spiking/discharge activity at 30 Hz which has been going on for a duration of 50 msec (sliding window duration).

The spike/potential detection indicator and the coefficient $c_{ij}$ value for the recording electrodes reflect the spatial information, while frequency of discharge determines other qualitative features (such as intensity) of stimulus. The duration of discharge (i.e., how long the signal keeps coming) determines duration of stimulus.

The sliding window duration "n" may be selected to optimize the operation of the spike/potential recognition algorithm and the overall performance of NBS. The default window size "n" may have a value of 50 msec in one embodiment.

6.5 Source Movement Template SMT

The $W_S$ matrix is the matrix that will be used in the comparison operation against a number of stored Source Movement Template matrices SMTs, to generate the high-level command(s). An SMT is identical in structure to the Window Matrix $W_S$ so a quick and efficient comparison can be performed.

The following illustrative source movement template matrix $SMT_1$ represents a particular movement command $M_1$.

$$SMT_1 = \begin{bmatrix} T_{11} = (1,0,0,0,0,0) & T_{12} = (1,1,30,50,0,0) & T_{13} = (1,0,0,0,0,0) & T_{14} = (1,0,0,0,0,0) \\ T_{21} = (1,0,0,0,0,0) & T_{22} = (1,1,40,50,0,0) & T_{23} = (1,1,20,50,0,0) & T_{24} = (1,1,10,50,0,0) \\ T_{31} = (1,0,0,0,0,0) & T_{32} = (1,1,90,50,0,0) & T_{33} = (1,1,30,50,0,0) & T_{34} = (1,1,30,50,0,0) \\ T_{41} = (1,0,0,0,0,0) & T_{42} = (1,0,0,0,0,0) & T_{43} = (1,1,30,50,0,0) & T_{44} = (1,1,40,50,0,0) \end{bmatrix}$$

In one embodiment, the weights (coefficients) in the source movement templates, which are the first digit in each entry, may be all set to the value "1".

The spiking/discharge duration for all the recording electrodes with spiking/discharge activity in the source movement template may be set to the sliding window duration, which is 50 msec in the preceding illustrative source movement template matrix $SMT_1$, if the sliding window duration is considered of a sufficient time resolution. That is, in one embodiment, the source template need only indicate the presence of spiking/discharge and its frequency in this 50 msec sliding window duration. The inclusion of the spiking/discharge duration is kept in this matrix for flexibility and future possible system enhancements.

The extracted $W_S$ matrix at each sample time is compared with a number of SMTs based on known best-match algorithms. There are a number of algorithms already developed in the area of text processing for the purpose of searching for a word, or pattern, of length "m" in a text of length "n", with "m"<"n". A match is declared when all the letters in the pattern find their match in some word in the larger text. A brute force algorithm implements the algorithm letter by letter from start to an end. Other variations of the brute force algorithm have also been developed over the years for the purpose of reducing the processing time and for optimization. The list of such algorithms is long and well documented in the literature.

For NBS, the match being performed includes spatial and temporal dimensions and is thus novel. Specifically, the best-match algorithm for NBS matches $W_S$ matrix with the SMTs taking into account the temporal information made of spike/spike presence, spike/spike frequency, and spiking/discharge duration, and the spatial (positional) information, for all the recording electrodes that are part of the matching pool. The matching pool of recording electrodes comprises all of the recording electrodes with their $c_{ij}$ value set to non-zero. Enhanced matching can take into account sub-threshold information.

In general, given the variations in the human anatomy it is unlikely that an exact 100% match will occur. Thus the matching process for NBS allows acceptable variations for each element within which a match is declared. For example, performing this multi-dimensional best-match operation between the preceding illustrative $W_S$ matrix and the preceding illustrative source movement template matrix $SMT_1$ will produce a most optimized match since the fourth column was removed from the evaluation criteria. The result is the generation and issuance of the HLMC $M_1$ that corresponds to the matched $SMT_i$ from the command module to the driver module at that particular time sample.

The movement command will include spatial information (which determines the driver modules to be activated) and the frequency (which determines the intensity of electrical stimulus to be delivered to the muscle). The duration of stimulation depends on the continued transmission of the micro-movement commands. If a no-match was determined (due to the low or unusual matching score), then no command will need to be generated and sent from the command module to the driver module(s).

6.6 Destination Movement Template DMT

In embodiments of the present invention, the driver module matches the received HLMC with one of the pre-stored Destination Movement Template (DMT) matrices stored in the system. These DMTs contain the digital representation for muscle stimulus (amperage) that needs to be applied at the target muscle(s) to achieve the desired muscle Push-Pull movement. Muscle drivers with electric probes located at the destination muscle convert this digital information to electrical current applied at the driver's probes for the CTI.

An electric stimulus for a muscle, for the CTI, has the following characteristics: (i) current value, or amperage, in mA, for a specific pulse width, in msec; and (ii) number of pulses, in the CTI.

In one embodiment, the DMT matrix is a linear list of elements represented as a matrix of one row and P columns, where entry 1 corresponds to probe 1, entry 2 corresponds to probe 2, . . . etc, as shown in the following structure of the DMT matrix.

$$DMT = [p_1\ p_2\ p_3 \ldots p_P]$$

Each element $p_i$ in the DMT matrix corresponds to a specific probe and comprises the following components: (i) number of pulses in the CTI duration; (ii) width of the pulses in this CTI; and (iii) value/strength of the pulses, in this CTI, in mA The following illustrative $DMT_1$ matrix is for a 4-probe driver module and a system wide CTI.

$$DMT_1 = [(2,1,50)(0,0,0)(4,1,30)(1,1,25)]$$

This preceding illustrative $DMT_1$ matrix translates into the stimulus depicted in Table 1.

TABLE 1

Stimulus From $DMT_1$ Matrix

| Probe | No. of Pulses Applied in the CTI | Pulse Width (msec) | Current Value (mA) |
|---|---|---|---|
| 1 | 2 | 1 | 50 |
| 2 | no stimulus | | |
| 3 | 4 | 1 | 30 |
| 4 | 1 | 1 | 25 |

Figure 6:
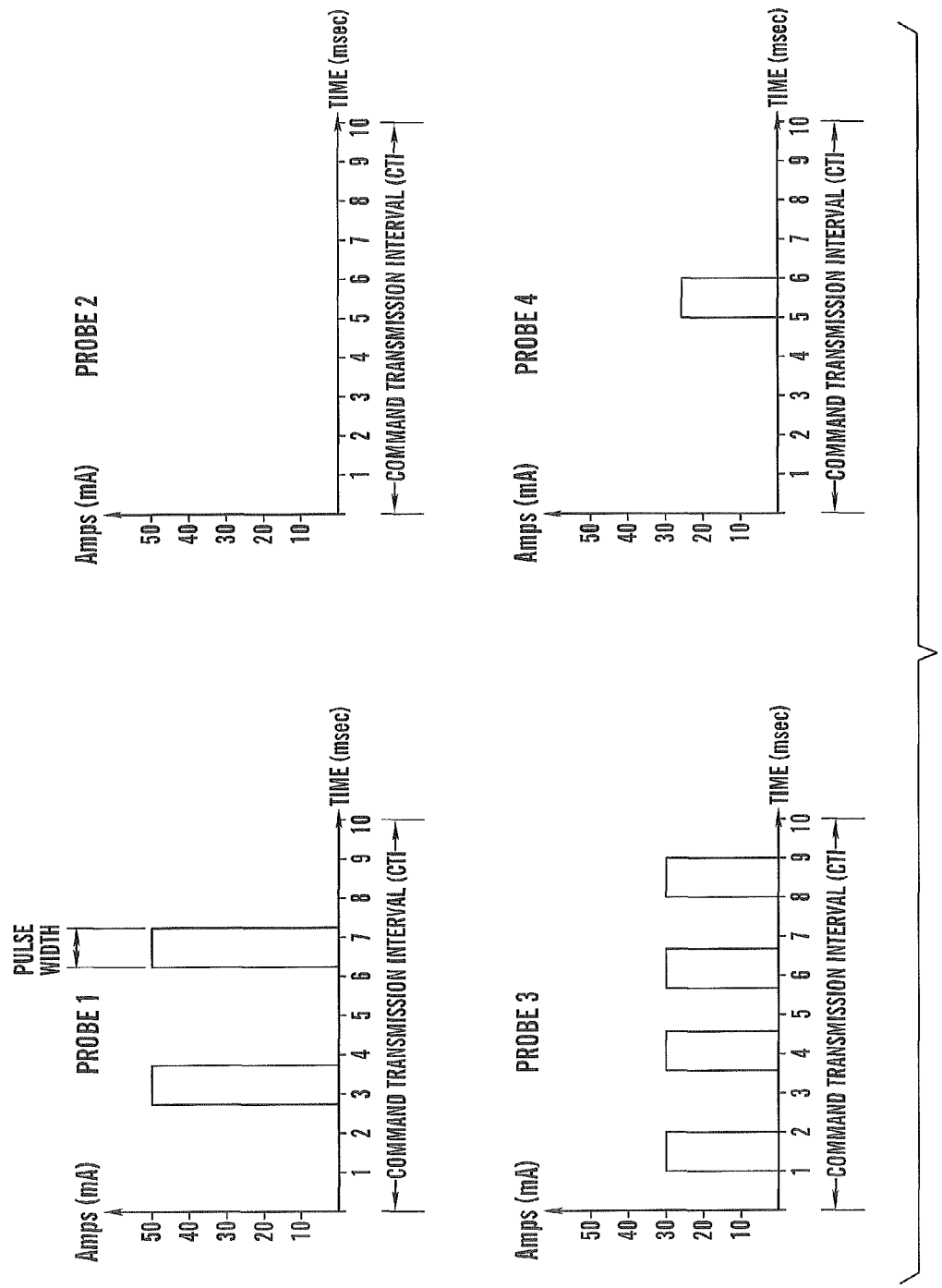
FIG. 6 is a graphical representation of an electric stimulus, in accordance with embodiments of the present invention.

FIG. 6 is a graphical representation of the electric stimulus depicted in Table 1, in accordance with embodiments of the present invention.

To reiterate, the HLMCs are generated by the command module and sent to the driver module every CTI period of time to induce a micro-movement action. In turn, the driver module applies the corresponding electrical stimulus via its probes for the duration of the CTI, according to the electrical specifications described in the destination movement templates. Thus, a particular movement command has an impact for the duration of CTI (in msec). Continuity is maintained ensuring that commands are sent every CTI, if a movement action is determined.

7. Movement Analysis

A movement in general involves multiple muscles, and thus requires stimulus at multiple locations to achieve the desired action.

Figure 7:
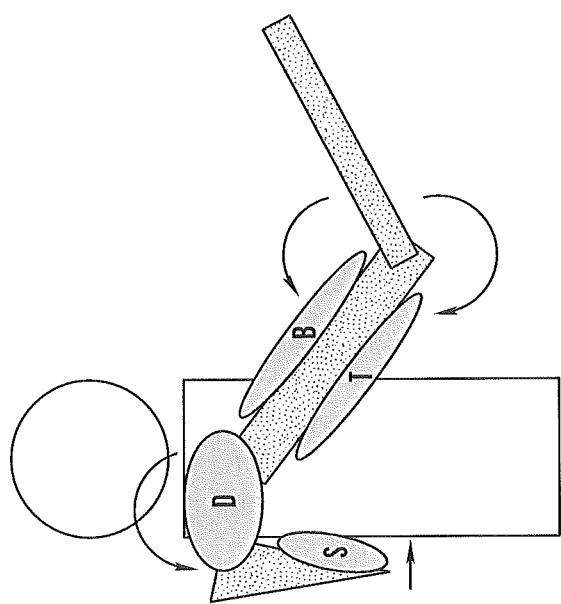
FIG. 7 depicts a functioning of muscle groups for a movement that includes push-pull with an arm, in accordance with embodiments of the present invention.

FIG. 7 depicts a functioning of muscle groups for a movement that includes push-pull with an arm, in accordance with embodiments of the present invention. Scapular muscles S will be active throughout the task to stabilize the shoulder and arm on the chest wall. The deltoid D (forward flexion of the shoulder) and triceps T (extension of the elbow) and the biceps B (flexion of the elbow) will be activated and deactivated in sequence. Thus for a push and a pull, the status of the muscle groups are as shown in Table 2.

TABLE 2

Status of Muscle Groups For Push or Pull

| MUSCLE GROUP | STATUS FOR PUSH | STATUS FOR PULL |
|---|---|---|
| Scapular muscles (S) | Active | Active |
| Deltoid (D) | Active | Relaxed |
| Triceps (T) | Active | Relaxed |
| Biceps (B) | Relaxed | Active |

Figure 8:
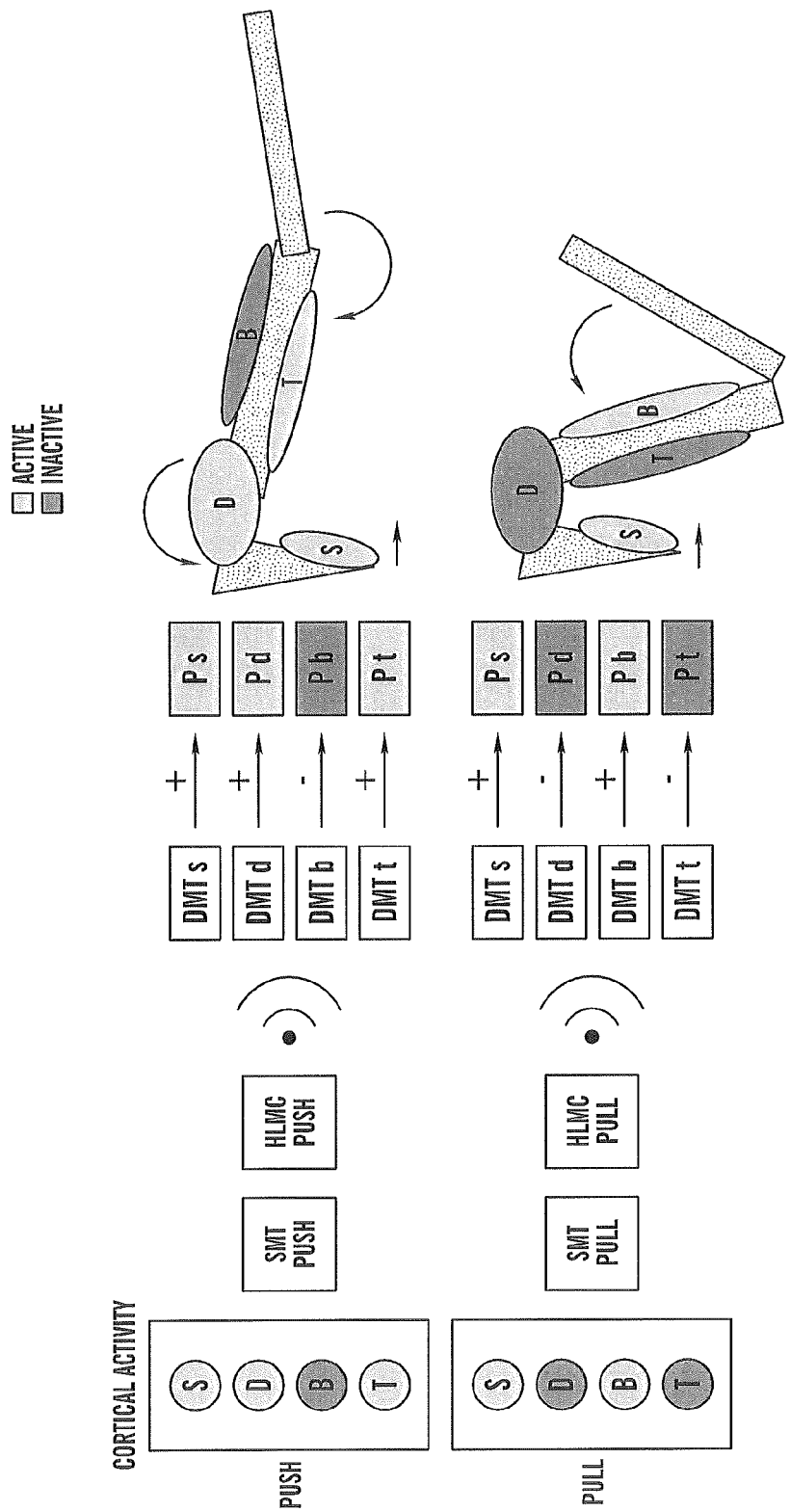
FIG. 8 is a schematic representation of push-pull movements starting at the cortex, in accordance with embodiments of the present invention.

FIG. 8 is a schematic representation of push-pull movements starting at the cortex, in accordance with embodiments of the present invention. Analyzing this motor function starting at the cortex, the following sequence of events will take place as depicted in FIG. 8.

When certain Upper Motor Neurons (UMNs) are activated, a pattern of neuronal firing is detected, a best-match algorithm correlates with the best available SMT, and one or several HLMCs are generated (based on which SMT was determined via application of the best-match algorithm to the $W_S$ matrix) and transmitted to the appropriate driver modules. The driver modules interpret the data and activate the probe. In FIG. 8, the "+" symbol denotes that the associated probe is activated and the "−" symbol denotes that the associated probe is not activated. For example in FIG. 8, DMTs activates probe Ps and DMTb does not activate probe Pb. The muscles are activated for as long as the commands are received.

8. Templates and Relation to Movement Commands

When NBS is implanted, the physician/technician performs system tuning and training functions to adapt the NBS system to the patient. The system tuning and training process will be used to match neural activity with the desired movement outcome, creating matching patterns on both ends of the system as follows.

The best coefficient $c_{ij}$ values for each of the entries in $A_S$ matrix are determined, which in one embodiment takes into account the position where the corresponding physical sensor array was implanted and the specific anatomy of the patient. This process is called micro tuning, as each element in the array is qualified with a weight that is unique to the position of that recording electrode in the patient.

After the best coefficient $c_{ij}$ values for each of the entries in $A_S$ matrix are determined, Source Movement Templates ($SMT_1$, $SMT_2$, $SMT_3$, etc.) are created by being tuned with the best values at each element in the array for the corresponding movement commands $M_1$, $M_2$, $M_3$, etc.

After the Source Movement Templates are created, a map between each source movement template $SMT_i$ and the corresponding high-level command HLMC $M_i$ is created.

In one embodiment, the collection of all tuned source movement templates $SMT_1$, $SMT_2$, $SMT_3$, etc., and the corresponding high-level movement commands (HLMCs) $M_1$, $M_2$, $M_3$, etc. is called the source pattern database and is stored in non-volatile memory in the command module.

In one embodiment, Destination Movement Templates $DMT_i$, $DMT_2$, $DMT_3$, etc., are created and stored in the Driver Module. This allows the translation of a particular HLMC $M_i$ into local stimulus via an electric probe attached to a muscle or a device. The stimulus is an electrical potential of certain intensity, frequency, and duration, which activates a specific muscle (or device) for the purpose of generating a specific motor task.

In one embodiment, the collection of all the movement commands $M_1$, $M_2$, $M_3$, etc. and their corresponding destination movement templates $DMT_i$, $DMT_2$, $DMT_3$, etc., along with their corresponding electrical stimulus is called the destination pattern database and is stored in non-volatile memory in the driver module.

9. Creation and Use of Templates

In the following discussion of creation and use of both source movement templates and destination movement templates, the sensor array is assumed to be recording intracortical neuronal activity. For nerve fiber recording, the same concept can be similarly applied.

9.1 Creation of the Source Movement Templates (SMTs)

A subject/person is asked to perform a specific movement, which will cause a number of UMNs to generate spiking activity. Using the sliding window method, the spatial and temporal information of the active neurons can be determined.

Initially, the subject repeatedly attempts to perform the same movement while spiking activities of each trial are compared. By comparing and analyzing the electrical activities from all the trials, a normalized spatial and temporal pattern of electrical activity for that specific movement is determined and stored as a Source Movement Template (SMT) in the command module.

9.2 Use of the Source Movement Templates (SMTs)

Subsequent attempts to perform a movement by the patient activate the same pool of UMNs, with some degree of variability and interference from other cortical neurons and with various intensity levels.

Use of a best-match algorithm allows the selection of the appropriate pre-stored SMT based on the detected pattern of movement by the patient.

The level of movement intensity is determined by examining the detected frequency values, and comparing with the typical/normalized source movement template. Consequently, a movement intensity factor is determined by the Command Module. The intensity factor is a multiplier that is communicated to the driver module, as part of the HLMC.

Consequently, one or more HLMCs is/are sent to the Driver Module(s), each with a specific movement command and intensity factor.

The HLMCs is/are wirelessly transmitted in the form of packets at the CTI rate (typically every 10 msec).

At the Driver Module, a command extractor (see CmdExtractor in FIG. 2) with a matching code intercepts and extracts the packet containing information from the corresponding HLMC.

9.3 Creation of the Destination Movement Templates (DMTs)

DMTs are location-specific to a muscle or a group of muscles. Their function is to determine the parameters of electrical muscle stimulation.

During system tuning and training, an HLMC is matched with a typical/normalized DMT with default stimulus values (e.g., 50 mA, 0.05 msec, for a particular electric probe). The values of stimulus are then tuned for best outcome and stored as a Destination Movement Template (DMT) in the Driver Module.

9.4 Use of the Destination Movement Templates (DMTs)

Command encoder (see CmdEnc in FIG. 2) will match the HLMC with a pre-stored typical/normalized DMT that contains the specific parameters of muscle stimulus (amperage and duration of stimulus).

A muscle driver located at the destination muscle converts the digital information to electrical current with matching parameters (e.g., 0-100 mA, and duration 0.05-1 msec).

Based on the movement intensity factor included in an HLMC, the Driver Module adjusts the stimulus intensity by increasing the stimulus frequency and/or raising the amperage value. Consequently, electrical stimulus is adjusted locally to achieve the intended force of contraction.

The duration of stimulation depends on the continued reception of commands from the Command Module.

The overall concept is to have two intelligent ends, with their local microprocessors and databases, communicating over a compact and efficient high-level command-based interface.

10. High Level Movement Commands (HLMC)

The movement commands $M_1$, $M_2$, $M_3$, etc. are encapsulated in packets for transmission over the wireless link. A packet is defined as follows:

Packet=(Preamble, Source Address, Destination Address, Security Key, Command Id, Intensity Factor, CRC)

where:

(1) Preamble, or start of frame, is transmitted first so that the receiver locks on the frame;

(2) Source Address is a structured field that uniquely identifies the patient unique ID and the source system unique ID;

(3) Destination Address is a structured field that uniquely identifies the patient unique ID, and the destination system unique ID;

(4) Security Key is a shared secret that allows for proper authentication of received messages, even if the addressing information matched;

(5) Command Id references a specific movement command $M_i$ on the system;

(6) Intensity Factor is a measure (a number/factor between 0 and 10) of the desired intensity for the selected movement; and (7) CRC is Cyclic Redundancy Check field, which is a widely used technique in transmission systems to validate/correct the payload of a transmission between two end points.

11. Data Representation and the High Level of Abstraction

Neural information collected at the nervous system is abundant and represents the lowest level of data abstraction. The present invention sorts through, processes, and summarizes the variety of local neural information, and raises the level of abstraction of the measured neural data to allow for the determination of the desired movement action.

Figure 9:
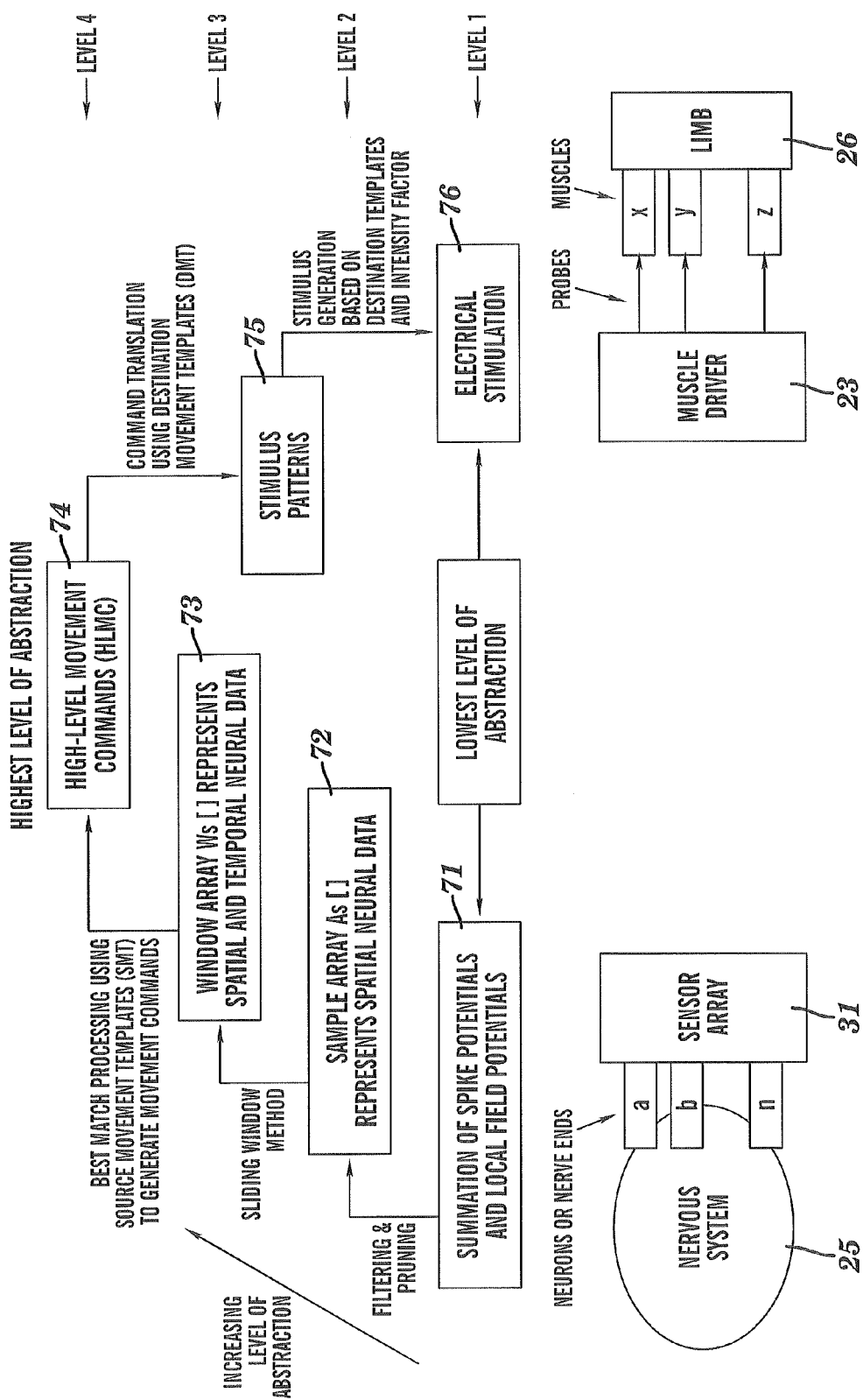
FIG. 9 depicts a hierarchy of NBS neural data representation at different stages from the source (Command Module) to the destination (Driver Module), in accordance with embodiments of the present invention.

FIG. 9 depicts a hierarchy of NBS neural data representation at different stages from the source (Command Module) to the destination (Driver Module), in accordance with the embodiments of the present invention. FIG. 9 starts with the lowest of level of abstraction (Level 1) at the source in the Command Module, and shows Levels 1, 2, 3, and 4 in a sequence of increasing levels of abstraction, until reaching the highest level of abstraction (Level 4), and then moving down the hierarchy until reaching the lowest level of abstraction at the destination in the Driver Module (Level 1), as shown. Steps 71-76 are sequentially performed.

At each intelligent end point (source and destination) a microprocessor (or a digital signal processor device) performs the required processing to move the data from one abstraction level to the next.

At Level 1 in step 71, which is the lowest level of abstraction (at the source in the Command Module), the summation of spike potentials and local field potentials are read by the sensor array recording electrodes.

Data, in the Command Module, is transformed from abstraction Level 1 in step 71 to abstraction Level 2 in step 72 by applying filtering and averaging techniques at each recording electrode, where the potentials/voltages are encoded into digital voltages for each sample and represented in the sample matrix $A_S$.

Data, in the Command Module, is transformed from abstraction Level 2 in step 72 to abstraction Level 3 in step 73 by applying the sliding window method for each recording electrode, where the temporal information is extracted and represented in the window matrix $W_S$.

Data, in the Command Module, is transformed from abstraction Level 3 in step 73 to abstraction level 4 in step 74, which is the highest level of data abstraction, by performing a best match algorithm for the totality of processed information between the window matrix $W_S$ and a number of source movement templates (SMTs) to create a high-level movement command (HLMC) for typical micro-movements at the command module. This HLMC is then transmitted over a wireless link to the driver module. The HLMC represents the highest level of data representation in the system.

Data, in the Driver Module, is transformed from abstraction Level 4 in step 74 to abstraction Level 3 in step 75 by translating the HLMCs into stimulus patterns representing a typical micro-movement using the destination templates.

Data, in the Driver Module, is transformed from abstraction Level 3 in step 75 to abstraction Level 1 in step 76 (Level 2 is skipped) by generating the electrical stimulus pattern based on the destination movement templates and the HLMC intensity factor using a local stimulus generator. This is the lowest level of data abstraction at the destination (Driver Module).

12. Aspects of the Neuro-Bridge System

The Neuro-Bridge System (NBS) of the present invention comprises the following aspects:

The Command Module is a miniature device that is implanted into the human body. It attaches to the cortex or the nerves (comprising of one or more sensor arrays, with tens to hundreds of recording electrodes) to sense the motor neurons or motor nerve fibers neural signals in the form of electrical action potentials.

The Command Module creates digitally coded high-level movement commands (HLMCs) corresponding to micro-movements based on tuned source movement templates and Neuro-Bridge sliding window method, which are then encapsulated in packets for transmission over a wireless medium to reach the Driver Module. This process tunes and adapts the NBS to fit a particular patient/host.

Minimum information (per data abstraction Level 4) is transported from the Command Module to the Driver Module to allow fast system response and to minimize the possibility of a transmission error. Only the determined command ID, movement intensity, and a few other parameters are transported, since both the Command Module and the Driver Module have stored copies of the movement templates and the command pairs.

The Driver Module is a small/miniature device that can be implanted into the human body attaching to the target muscle(s) or device. It is designed so it can receive commands over a wireless medium and provide the proper stimulus based on the received command.

It is possible to operate the Command Module and the Driver Module using small voltages via miniature batteries.

The NBS is characterized by intelligent ends, micro-movements, movement templates, sliding window method, and optimized wireless interface carrying high-level commands.

13. Features of the Present Invention

A miniature neuro-electrical wireless system referred to as the Neuro-Bridge System (NBS) can be implanted in the human body as a patch or a bridge to a partially damaged nervous system. The NBS may comprise three main modules: a Command Module (CM) that attaches to the nervous system, a wireless transport system, and a Driver Module (DM) that attaches to the target organ. The system operates based on intelligent end points, high-level of data abstraction via the creation of Sample Matrix $A_S$, the Window Matrix $W_S$, and the high-level movement command (HLMC), and operating based on movement templates and the Neuro-Bridge sliding window method.

In one embodiment, the brain/nervous system activities may be represented at a high level of data abstraction via two matrices: the Sample Matrix $A_S$ that captures the nervous system spatial electrical potential information and the Window Matrix $W_S$ that captures the nervous system temporal electrical potential information. A Neuro-Bridge sliding window method is used to generate the $W_S$ matrix from multiple consecutive readings of the $A_S$ matrix to add the temporal information to the spatial information collected in matrix $A_S$.

The Command Module (CM) may include one or multiple physical sensor arrays with recording electrodes attaching to the nervous system, with respect to the following embodiments:

The Command Module:
(i) records neural signals periodically and at regular intervals;
(ii) collects patterns of neural signals from each recording electrode in the form of electrical action potentials generated by neurons or nerve fibers;
(iii) converts the neural signals detected from each recording electrode to coded digital signals; and
(iv) applies filtering and averaging techniques to clean the signals from noise and non-essential information; stores spatial coded digital signals for each recording electrode, for each sample, in its corresponding entry in the sample matrix $A_S$.

For a multi-sensor array system, the command module uses the Sensor Map Matrix S to map the recording electrodes from the different physical arrays into a virtual sensor array.

The Command Module collects the information from the virtual sensor array into the Sample Matrix $A_S$.

The Command Module correlates the spatial data collected from the latest sample matrix $A_S$ with the spatial data collected from "n−1" previous sample matrices to incorporate the temporal dimension into the measured neural activity.

At each sampling period for each recording electrode, the Command Module runs the Neuro-Bridge sliding window method described herein to generate the sliding window matrix Ws, where pattern recognition techniques are applied for "n" consecutive sample matrices $A_S$, within the sliding window time, to add the temporal information to the spatial information.

At each sampling period, the Command Module may extract and represent spiking/discharge information for each recording electrode in the corresponding entry in the $W_S$ matrix.

At each sampling period, the Command Module may compare the totality of the spatial and temporal information that is generated and stored in the $W_S$ matrix with pre-defined, pre-stored, typical/normalized source movement templates using best-match algorithms.

Taking into account the values in the Coefficients Matrix $C_S$, if a match within a period of time defined as the Command Transmission Interval (CTI), within a level of acceptable and settable system variation, is determined between the real-time generated $W_S$ matrix and one of the stored source movement templates (SMTs), the Command Module generates the high level movement command (HLMC) corresponding to a specific micro-movement, which may include a specific movement intensity factor.

The Command Module encapsulates the HLMC in a packet which may include proper framing, source address, destination address, data integrity, and data security fields; and sends the packet over the secured wireless link.

The Driver Module (DM):
(i) attaches to the target muscle(s) or robotic device/instrument or electronic device, where the driver module receives HLMCs over the wireless transport system;
(ii) translates the HLMCs into a corresponding digital stimulus for a typical micro-movement based on pre-defined and pre-stored typical/normalized destination movement templates (DMTs); and
(iii) converts the digital stimulus to electrical analog stimulus, which may take into account a movement intensity factor, and then delivers the electrical analog stimulus to the target muscles or robotic/electronic device or instrument.

In one embodiment, the Sample Matrix $A_S$ may include or consist of "x" entries representing collected measurements, each associated with a recording electrode in the virtual sensor array of "x" pins/electrodes, which in turn is a reflection of a specific recording electrode from a specific physical sensor array. Each entry in the sample matrix $A_S$ may include or consist of two components: (i) the actual measured action potential, $v_{ij}$, at that sample, in mV; (ii) a multiplier as a coefficient $c_{ij}$ that is associated with that recording electrode so to allow the system to amplify or suppress the measured reading on a particular recording electrode to account for any noise or other variations.

In one embodiment, the coefficients take into considerations two key factors: the somatotopic organization of the nervous system and inevitable variability from one person to another. Therefore, the coefficients are tuned (re-programmed) before and after implantation to better suit the anatomy and function of the patient. This is referred to as the process of tuning and training the system and it shall be possible over a wireless communication link to the command module.

In one embodiment, the sliding window matrix $W_S$ may include or consist of "x" entries $w_{ij}$ corresponding to the size "x" of the sample matrix $A_S$, where each entry is associated with a recording electrode in the virtual sensor array. Each entry $w_{ij}$ in the $W_S$ matrix is a multi-dimensional entity that may comprise some or all of the following components:
- (i) weight of this element in the matching process taking into account the coefficient $c_{ij}$ in the Sample Matrix $A_S$;
- (ii) spike/potential presence indicator on that recording electrode;
- (iii) spike/potential frequency in Hz if spiking/discharge activity was detected/recognized in this window on that recording electrode;
- (iv) spiking/discharge duration in msec if spiking/discharge activity was detected/recognized in this window, on that recording electrode;
- (v) sub-threshold potential value representing the summation of LFPs in milli Volt on that recording electrode;
- (vi) sub-threshold potential duration if recognized by the extraction algorithm on that recording electrode.

In one embodiment, the sliding window advances one sample time, causing the creation of a new sample matrix $A_S$ and the generation of another set of multi-dimensional entries in the Window Matrix $W_S$.

In one embodiment, a library of typical/normalized source movement templates (SMTs) and their corresponding high-level movement commands (HLMCs) is created and stored in the non-volatile memory of the command module.

In one embodiment, a library of typical/normalized destination movement templates (DMTs) is created and stored in the non-volatile memory of the driver module. These DMTs are associated with the HLMCs.

In one embodiment, the source movement templates (SMTs) can be tuned, adapted, and optimized to the specific patient's needs as part of the system training phase performed by the physician when the system is implanted, or afterward as part or periodic tuning and system re-retraining sessions.

In one embodiment, the destination movement templates (DMTs) can be tuned, adapted, and optimized to the specific patient's needs as part of the system training phase performed by the physician when the system is implanted, or afterward as part or periodic tuning and system re-retraining sessions.

14. Method for Connecting an Impaired Nervous System to Muscle(s)

Figure 10:
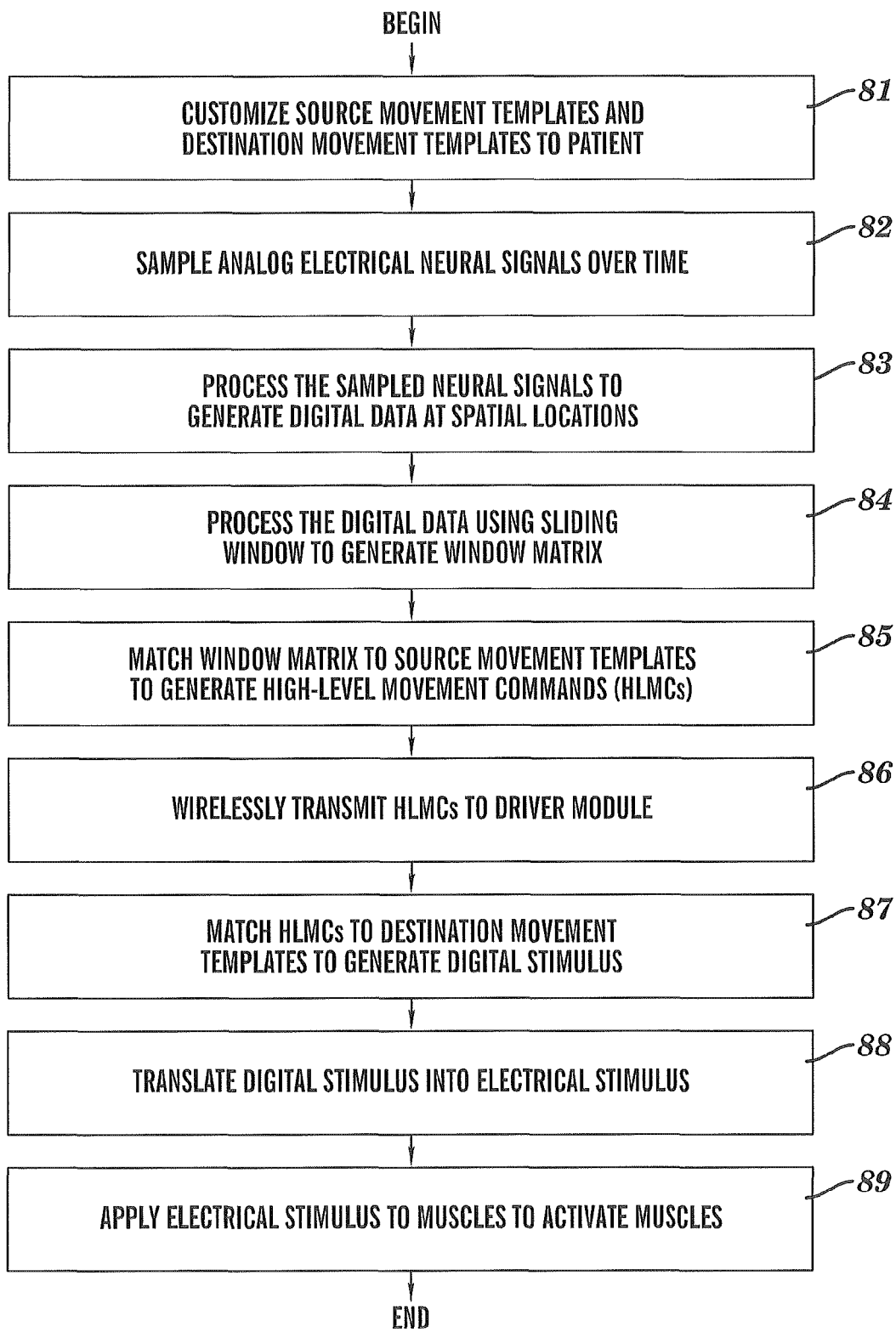
FIG. 10 is a flow chart depicting a method for connecting an impaired nervous system of a patient to a destination target, in accordance with embodiments of the present invention.

FIG. 10 is a flow chart depicting a method for connecting an impaired nervous system of a patient to a destination target, in accordance with embodiments of the present invention. FIG. 10 comprises steps 81-89.

In step 81, both source movement templates and destination movement templates are customized to the patient.

In step 82, a Command Module samples analog electrical neural signals over time at a sampling period. The neural signals have been generated by neurons or nerve fibers of the patient and have been sampled at each spatial location of a plurality of spatial locations within the patient's body. The Command Module is a first device implanted within the patient's body.

In step 83, the Command Module processes the sampled analog electrical neural signals to generate digital data specific to the spatial locations.

In step 84, the Command Module processes the digital data in the sliding window to generate a window matrix. The Command Module uses a sliding window process which advances in time, in step with the sampling period. The sliding window has a sliding window time duration that exceeds the sampling period. The sliding window encompasses the digital data over the sliding window time duration. Each element of the window matrix comprises parameters relating to electrical spiking/discharge activity at the spatial locations over the sliding window time duration.

In step 85, the Command Module matches parameters in the window matrix to the stored information in the source movement templates to generate at least one high-level movement command relating to electrically activating the destination target. The destination target is a muscle of the patient, a group of muscles of the patient, or a robotic device.

In step 86, the at least one high-level movement command is wirelessly transmitted to at least one Driver Module at a command transmission interval of time that exceeds the sampling period and is less than the sliding window time duration. The at least one Driver Module is at least one second device implanted within the patient's body and attached to the destination target. The at least one Driver Module is one Driver Module or multiple Driver Modules associated with and controlled by a single Command Module.

In step 87, the at least one Driver Module matches the at least one high-level movement command to destination movement templates to generate at least one digital stimulus.

In step 88, the at least one Driver Module translates the at least one digital stimulus into at least one electrical stimulus, In step 89, the at least one Driver Module applies the at least one electrical stimulus to the destination target.

In one embodiment, the Command Module comprises a plurality of sensor arrays, wherein a recording electrode exists at each element of each sensor array, and wherein the method further comprises generating a sensor mapping matrix consisting of a plurality of sub-matrices, wherein each sensor array of the plurality of sensor arrays corresponds to an associated sub-matrix of the plurality of sub-matrices, and wherein said generating the sensor mapping matrix comprises loading each sensor array into its associated sub-matrix.

In one embodiment, (i) the Command Module comprises a sensor array, said sensor array comprising a plurality of elements; (ii) a recording electrode exists at each element of the sensor array; (iii) processing the sampled analog electrical neural signals comprises organizing the sampled analog electrical neural signals into a sampling matrix that comprises the digital data; (iv) each element of the sampling matrix corresponds to a corresponding element of the sensor array and to the recording electrode at the corresponding element of the sensor array; and (v) each element of the sampling matrix comprises a product of an electrical potential measured at the recording electrode at the corresponding element of the sensor array and a coefficient whose value is zero or a positive real number.

In one embodiment, the value of the coefficient is zero for at least one recording electrode in the sensor array, which results in the electrical potential measured at the at least one recording electrode being ignored.

In one embodiment, the value of the coefficient exceeds zero and is less than one for at least one recording electrode in the sensor array, which results in the electrical potential measured at the at least one recording electrodes being attenuated.

In one embodiment, the value of the coefficient exceeds one for at least one recording electrode in the sensor array, which results in the electrical potential measured at the at least one recording electrode being amplified.

In one embodiment, each element of the window matrix is associated with an associated element of the sensor array and with the recording electrode at the associated element of the sensor array, wherein each element of the window matrix comprises: (i) the coefficient; (ii) a spike/potential presence indicator specifying whether an electrical spike/potential has been or has not been detected in the sliding window at the recording electrode at the associated element of the sensor array; and (iii) a spike/potential frequency and duration of the electrical spike/potential in the sliding window, if the electrical spike/potential has been detected in the sliding window.

In one embodiment in which the destination target is the muscle or group of muscles, the at least one Driver Module comprises at least one electric probe coupled to the muscle or the group of muscles, wherein activating the muscle or the group of muscles comprises the at least one electric probe electrically activating the muscle or the group of muscles for the duration of the command transmission interval of time. In one embodiment, the at least one electrical stimulus is characterized by a total number of electrical pulses in the command transmission interval of time, a value of electrical current for each pulse, and a pulse width of each pulse.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method for connecting an impaired nervous system of a patient to a destination target, said method comprising:

a command module sampling analog electrical neural signals over time at a sampling period, said neural signals having been generated by neurons or nerve fibers of the patient and having been sampled at each spatial location of a plurality of spatial locations within the patient's body, said command module being a first device implanted within the patient's body;

said command module processing the sampled analog electrical neural signals to generate digital data specific to the spatial locations;

said command module using a sliding window process to generate a sliding window which advances in time in step with the sampling period, said sliding window having a sliding window time duration that exceeds the sampling period, said sliding window encompassing the digital data over the sliding window time duration;

said command module processing the digital data in the sliding window to generate a window matrix, each element of the window matrix comprising parameters relating to electrical spiking/discharge activity at the spatial locations over the sliding window time duration;

said command module matching the parameters in the window matrix to stored information in source movement templates to generate at least one high-level movement command relating to electrically activating the destination target, said destination target being a muscle of the patient, a group of muscles of the patient, or a robotic device;

wirelessly transmitting the at least one high-level movement command to at least one driver module at a command transmission interval of time that exceeds the sampling period and is less than the sliding window time duration, said at least one driver module being at least one second device implanted within the patient's body and attached to the destination target;

said at least one driver module matching the at least one high-level movement command to destination movement templates to generate at least one digital stimulus;

said at least one driver module translating the at least one digital stimulus into at least one electrical stimulus;

said at least one driver module applying the at least one electrical stimulus to the destination target, which activates the destination target.

2. The method of claim 1, wherein the command module comprises a plurality of sensor arrays, wherein a recording electrode exists at each element of each sensor array, and wherein the method further comprises:

generating a sensor mapping matrix consisting of a plurality of sub-matrices, wherein each sensor array of the plurality of sensor arrays corresponds to an associated sub-matrix of the plurality of sub-matrices, and wherein said generating the sensor mapping matrix comprises loading each sensor array into its associated sub-matrix.

3. The method of claim 1, wherein the command module comprises a sensor array, said sensor array comprising a plurality of elements, wherein a recording electrode exists at each element of the sensor array, wherein said processing the sampled analog electrical neural signals comprises organizing the sampled analog electrical neural signals into a sampling matrix that comprises the digital data, wherein each element of the sampling matrix corresponds to a corresponding element of the sensor array and to the recording electrode at the corresponding element of the sensor array, and wherein each element of the sampling matrix comprises a product of an electrical potential measured at the recording electrode at the corresponding element of the sensor array and a coefficient whose value is zero or a positive real number.

4. The method of claim 3, wherein the value of the coefficient is zero for at least one recording electrode in the sensor array, which results in the electrical potential measured at the at least one recording electrode being ignored.

5. The method of claim 3, wherein the value of the coefficient exceeds zero and is less than one for at least one recording electrode in the sensor array, which results in the electrical potential measured at the at least one recording electrode being attenuated.

6. The method of claim 3, wherein the value of the coefficient exceeds one for at least one recording electrode in the sensor array, which results in the electrical potential measured at the at least one recording electrode being amplified.

7. The method of claim 3, wherein the sliding window process generates the window matrix from consecutive sample matrices over the sliding window duration and performs correlation and feature extraction functions in real time to generate the elements of the window matrix, wherein each element of the window matrix is associated with a corresponding element of the sensor array and with the recording electrode at the corresponding element of the sensor array, and wherein each element of the window matrix comprises:

the coefficient;

a spike/potential presence indicator specifying whether an electrical spike/potential has been or has not been detected in the sliding window at the recording electrode at the corresponding element of the sensor array; and a spike/potential frequency and duration of the electrical spike/potential in the sliding window, if the electrical spike/potential has been detected in the sliding window.

8. The method of claim 1, wherein the destination target is the muscle or the group of muscles, and wherein the at least one driver module comprises at least one electric probe coupled to the muscle or the group of muscles, and wherein said activating comprises said at least one electric probe electrically activating the muscle or the group of muscles for the duration of the command transmission interval of time.

9. The method of claim 8, wherein the at least one electrical stimulus is characterized by a total number of electrical pulses in the command transmission interval of time, a value of electrical current for each pulse, and a pulse width of each pulse.

10. The method of claim 1, wherein the method further comprises prior to said sampling analog electrical neural signals over time;
customizing the source movement templates to the patient; and
customizing the destination movement templates to the patient.

11. A neuro-bridge system comprising a command module and at least one driver module, said system configured to implement a method for connecting an impaired nervous system to a destination target, said method comprising:
said command module sampling analog electrical neural signals over time at a sampling period, said neural signals having been generated by neurons or nerve fibers of the patient and having been sampled at each spatial location of a plurality of spatial locations within the patient's body, said command module being a first device implanted within the patient's body;
said command module processing the sampled analog electrical neural signals to generate digital data specific to the spatial locations;
said command module using a sliding window process to generate a sliding window which advances in time in step with the sampling period, said sliding window having a sliding window time duration that exceeds the sampling period, said sliding window encompassing the digital data over the sliding window time duration;
said command module processing the digital data in the sliding window to generate a window matrix, each element of the window matrix comprising parameters relating to electrical spiking/discharge activity at the spatial locations over the sliding window time duration;
said command module matching the parameters in the window matrix to stored information in source movement templates to generate at least one high-level movement command relating to electrically activating the destination target, said destination target being a muscle of the patient, a group of muscles of the patient, or a robotic device;
wirelessly transmitting the at least one high-level movement command to said at least one driver module at a command transmission interval of time that exceeds the sampling period and is less than the sliding window time duration, said at least one driver module being at least one second device implanted within the patient's body and attached to the destination target;
said at least one driver module matching the at least one high-level movement command to destination movement templates to generate at least one digital stimulus;
said at least one driver module translating the at least one digital stimulus into at least one electrical stimulus;
said at least one driver module applying the at least one electrical stimulus to the destination target, which activates the destination target.

12. The system of claim 11, wherein the command module comprises a plurality of sensor arrays, wherein a recording electrode exists at each element of each sensor array, and wherein the method further comprises:
generating a sensor mapping matrix consisting of a plurality of sub-matrices, wherein each sensor array of the plurality of sensor arrays corresponds to an associated sub-matrix of the plurality of sub-matrices, and wherein said generating the sensor mapping matrix comprises loading each sensor array into its associated sub-matrix.

13. The system of claim 11,
wherein the command module comprises a sensor array, said sensor array comprising a plurality of elements,
wherein a recording electrode exists at each element of the sensor array,
wherein said processing the sampled analog electrical neural signals comprises organizing the sampled analog electrical neural signals into a sampling matrix that comprises the digital data,
wherein each element of the sampling matrix corresponds to a corresponding element of the sensor array and to the recording electrode at the corresponding element of the sensor array, and
wherein each element of the sampling matrix comprises a product of an electrical potential measured at the recording electrode at the corresponding element of the sensor array and a coefficient whose value is zero or a positive real number.

14. The system of claim 13, wherein the value of the coefficient is zero for at least one recording electrode in the sensor array, which results in the electrical potential measured at the at least one recording electrode being ignored.

15. The system of claim 13, wherein the value of the coefficient exceeds zero and is less than one for at least one recording electrode in the sensor array, which results in the electrical potential measured at the at least one recording electrode being attenuated.

16. The system of claim 13, wherein the value of the coefficient exceeds one for at least one recording electrode in the sensor array, which results in the electrical potential measured at the at least one recording electrode being amplified.

17. The system of claim 13, wherein the sliding window process generates the window matrix from consecutive sample matrices over the sliding window duration and performs correlation and feature extraction functions in real time to generate the elements of the window matrix, wherein each element of the window matrix is associated with a corresponding element of the sensor array and with the recording electrode at the corresponding element of the sensor array, and wherein each element of the window matrix comprises:
the coefficient;
a spike/potential presence indicator specifying whether an electrical spike/potential has been or has not been detected in the sliding window at the recording electrode at the corresponding element of the sensor array; and
a spike/potential frequency and duration of the electrical spike/potential in the sliding window, if the electrical spike/potential has been detected in the sliding window.

18. The system of claim 11, wherein the destination target is the muscle or the group of muscles, and wherein the at least one driver module comprises at least one electric probe coupled to the muscle or the group of muscles, and wherein said activating comprises said at least one electric probe electrically activating the muscle or the group of muscles for the duration of the command transmission interval of time.

19. The system of claim 18, wherein the at least one electrical stimulus is characterized by a total number of electrical pulses in the command transmission interval of time, a value of electrical current for each pulse, and a pulse width of each pulse.

20. The system of claim 11, wherein the method further comprises prior to said sampling analog electrical neural signals over time;

customizing the source movement templates to the patient; and customizing the destination movement templates to the patient.

* * * * *